US012779239B2

(12) United States Patent
Velasco Valcke

(10) Patent No.: US 12,779,239 B2
(45) Date of Patent: Nov. 3, 2026

(54) MAGNETIC STIMULATION METHOD AND MACHINE

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: PANACEA QUANTUM LEAP TECHNOLOGY LLC, Dallas, TX (US)

( * ) Notice: Subject to any disclaimer, the term of this patent is extended or adjusted under 35 U.S.C. 154(b) by 1194 days.

(21) Appl. No.: 17/442,980

(22) PCT Filed: Mar. 28, 2020

(86) PCT No.: PCT/IB2020/052981
§ 371 (c)(1),
(2) Date: Sep. 24, 2021

(87) PCT Pub. No.: WO2020/194278
PCT Pub. Date: Oct. 1, 2020

(65) Prior Publication Data

US 2022/0176144 A1 Jun. 9, 2022

(30) Foreign Application Priority Data

Mar. 28, 2019 (CO) ........................ NC2019/0003100

(51) Int. Cl.
*A61N 2/02* (2006.01)
*A61N 2/12* (2006.01)

(52) U.S. Cl.
CPC ................. *A61N 2/02* (2013.01); *A61N 2/12* (2013.01); *A61H 2201/10* (2013.01)

(58) Field of Classification Search
CPC . A61N 2/02; A61N 2/12; A61N 2/006; A61H 2201/10
(Continued)

(56) References Cited

U.S. PATENT DOCUMENTS 4,276,529 A 6/1981 Heinzerling et al.
5,084,003 A 1/1992 Susic
(Continued)

FOREIGN PATENT DOCUMENTS

CN 107174742 A 9/2017
CO 2017011756 A1 5/2019
(Continued)

OTHER PUBLICATIONS

INAPI, International Search Report for International Patent Application No. PCT/IB2020/052981, mailed Jul. 2, 2020.
(Continued)

*Primary Examiner* — Sunita Reddy
(74) *Attorney, Agent, or Firm* — Talem IP Law, LLP

(57) ABSTRACT

The present disclosure relates to non-invasive magnetic stimulation of tissue using machines, and methods where a magnetic field moves relative to the tissue.
The machine includes a coil that generates a magnetic field and a first displacement mechanism. This mechanism moves the connected coil around the target tissue following a specific pattern during stimulation. A corresponding method discloses generating the magnetic field and dynamically moving the coil in a predetermined motion pattern around the tissue for stimulating the tissue.

10 Claims, 16 Drawing Sheets

(58) Field of Classification Search
USPC ........................................................ 600/9–15
See application file for complete search history.

(56) References Cited

U.S. PATENT DOCUMENTS

| | | | | |
|---|---|---|---|---|
| 5,989,178 | A | 11/1999 | Chiu | |
| 6,004,257 | A | 12/1999 | Jacobson | |
| 6,099,459 | A * | 8/2000 | Jacobson | A61N 2/02 128/897 |
| 8,088,058 | B2 | 1/2012 | Juliana et al. | |
| 9,974,519 | B1 | 5/2018 | Schwarz et al. | |
| 2003/0094510 | A1* | 5/2003 | Laughlin | A61K 8/355 239/200 |
| 2004/0097781 | A1* | 5/2004 | Ichikawa | A61N 5/02 600/9 |
| 2006/0047316 | A1* | 3/2006 | Fischell | A61N 2/02 607/1 |
| 2006/0161039 | A1* | 7/2006 | Juliana | A61N 2/006 600/9 |
| 2009/0083071 | A1* | 3/2009 | Phillips | A61N 2/06 705/2 |
| 2009/0216067 | A1* | 8/2009 | Lebosse | A61B 34/76 600/13 |
| 2009/0227830 | A1* | 9/2009 | Pillutla | A61N 2/02 600/13 |
| 2011/0125203 | A1 | 5/2011 | Simon et al. | |
| 2011/0130617 | A1* | 6/2011 | Dennis | A61N 2/02 600/14 |
| 2013/0211181 | A1* | 8/2013 | Schmidt | A61N 2/002 600/13 |
| 2013/0225914 | A1* | 8/2013 | Soza | A61B 5/398 600/26 |
| 2015/0157873 | A1 | 6/2015 | Sokolowski | |
| 2015/0230810 | A1* | 8/2015 | Creighton | A61K 41/0028 604/518 |
| 2016/0250494 | A1 | 9/2016 | Sakaki et al. | |
| 2017/0291039 | A1 | 10/2017 | Jacobson et al. | |
| 2018/0125416 | A1 | 5/2018 | Schwarz | |
| 2019/0321472 | A1* | 10/2019 | Creighton | A61N 2/06 |
| 2021/0093339 | A1* | 4/2021 | Creighton | A61B 17/22004 |
| 2023/0043685 | A1* | 2/2023 | Helekar | A61B 5/291 |

FOREIGN PATENT DOCUMENTS

| | | | |
|---|---|---|---|
| JP | 2009261814 | A | 11/2009 |
| WO | WO-2000/013749 | A1 | 3/2000 |
| WO | WO-2005/094940 | A1 | 10/2005 |

OTHER PUBLICATIONS

INAPI, Written Opinion for International Patent Application No. PCT/IB2020/052981, mailed Jul. 2, 2020.
Office Action issued in Japanese Application No. 2024-212353, mailed Feb. 24, 2026, 9 pages.

* cited by examiner

MAGNETIC STIMULATION METHOD AND MACHINE

CROSS-REFERENCE TO RELATED APPLICATIONS

This application is the National Stage of International Application No. PCT/IB2020/052981 filed Mar. 28, 2020, and claims benefit of Colombian Patent Application No. NC2019/0003100 filed Mar. 28, 2019, the disclosures each of which are incorporated herein by reference in their entirety.

TECHNICAL FIELD

The present disclosure is related to machines and methods for the magnetic stimulation of tissues and more specifically to machines and methods for the magnetic stimulation of tissues which are non-invasive for the tissue being stimulated.

BACKGROUND

There are medical ailments that are treated or diagnosed through the application of a time-varying magnetic field to an affected portion of a patient's body. Muscle tissue cells, nervous tissue cells, living tissue or a conductive biological tissue respond to magnetic stimuli and, in general, to electromagnetic fields.

When a time-varying magnetic field is applied to a body, an electric current is induced to a portion of the body, thus, the cells that make up the biological tissue of said portion of the body can be stimulated by polarizing or depolarizing them. Also, it is possible to use a time-varying magnetic field to contract muscle tissue as if it were stimulation at the nervous tissue level.

Due to this interaction between the time-varying magnetic field and the biological tissue, magnetic stimulation could be used in the rehabilitation of injured or paralyzed muscle groups, therapies where the peripheral nerve is stimulated, for pain relief, revascularization stimulation, wound healing, tissue movement and bone growth or bone regeneration. One area of particular interest is the treatment of neuropsychiatric disorder depression. These include conditions such as depression, schizophrenia, mania, obsessive-compulsive disorder, panic disorders, among others. Another area is the investigation of the response of tissues to their magnetic stimulation.

Magnetic stimulation with time-varying magnetic fields can be applied invasively or non-invasively. With the invasive application, it is necessary to break healthy tissues surrounding a tissue of interest to be able to access said tissue of interest, which may cause additional complications to those produced by the tissue of interest, so in some cases it is inadvisable to use the application of magnetic stimulation invasively.

On the other hand, with the application of time-varying magnetic fields in a non-invasive way, the tissues are polarized or depolarized by the induction of small magnetic fields in the cells that make up the tissue without the need for tissue intervention, so it is advisable, which does not generate the adverse effects of a surgical intervention in tissues surrounding the tissue of interest.

The application of time-varying magnetic fields in a non-invasive way is carried out, for example, by means of energy pulses. To generate a magnetic pulse that is capable of providing a therapeutic effect in a patient, TMS (transcranial magnetic stimulation), ITMS (repetitive transcranial magnetic stimulation) and magneto-convulsive therapy (MCT) treatments require a large amount of electrical energy, generally several hundred Joules (J) per pulse.

Thus, in the state of the art devices and methods for the magnetic stimulation of tissues are disclosed, such as those disclosed by U.S. Pat. No. 5,989,178 A and patent US 2011/0125203 A1.

U.S. Pat. No. 5,989,178 A discloses a magnetic stimulation device and method used to accelerate blood circulation. The device is a magnetic ring that includes a ring with a pair of permanent magnets positioned in such a way that the magnetic field of the two magnets is reinforced inside the ring. The method involves placing the ring on a person's fingers/toes to promote improvement of the person's blood circulation. In particular, a polarity direction must be respected when using a magnetic ring, for example: in a particular embodiment, if a ring is worn on the little finger of the left hand, the magnetic north of the ring must point in the direction of the part lower finger; if on the contrary, worn on the right hand so the magnetic north of the ring should point towards the top of the Little finger.

For its part, document US 2011/0125203 A1 discloses devices and systems for the non-invasive treatment of medical conditions delivering energy in the form of pulses to body tissues for therapeutic purposes. The device is an electrical coil connected to a source of electrical energy. One of the objectives of the invention is to form an elongated electric field that can be oriented parallel to a particular nervous tissue. However, the devices and systems disclosed in document US 2011/0125203 A1 retain a position with respect to the tissue, so they must be located in a very precise point, and in a very particular orientation, which requires a very high level of specialized personnel to stimulate tissue.

In the present document, stimulation of a biological tissue refers to administering energy to said biological tissue to induce certain changes in the characteristics of said biological tissue, such as the impedance response of the tissue, the vascularization of the tissue, the temperature of the tissue, tissue health, tissue growth rate, among others.

BRIEF DESCRIPTION OF THE SPECIFICATION

The present disclosure relates to machines and methods for magnetic stimulation of tissues, and more specifically to machines and methods for magnetic stimulation of tissues that are non-invasive to the tissue being stimulated.

One of the disclosed embodiments is a magnetic stimulation machine, comprising: a coil that generates a magnetic field; and a first displacement mechanism connected to the coil and to a bearing surface; where the first displacement mechanism moves the coil around the tissue to stimulate it.

In a particular embodiment, the first displacement mechanism is connected to the coil by means of an angular actuator; where the angle actuator rotates the coil to change the direction of the magnetic field.

In another particular embodiment of the disclosed machine, the coil is a Helmholtz coil arrangement.

In a specific embodiment, the first displacement mechanism is selected from the group that includes winches, cranes, pneumatic, hydraulic, mechanical or electromechanical actuation cylinders, single-acting cylinders, double-acting cylinders, gantries provided with chain, cable, or belt, where the hoists can include skids that allow a movement orthogonal to the longitudinal direction, scissor lifts, trolley-guide mechanisms and combinations thereof.

Optionally, in embodiments of the machine of the disclosure, the first displacement mechanism is a carriage-guide mechanism that includes a first guide connected to the bearing surface, a first carriage movably coupled to the first guide, and a first motive mechanism connected to the first carriage, where the first motive mechanism moves the first carriage along the first guide.

Alternatively, the first drive mechanism includes a braking device connected to the first drive mechanism.

In an alternative embodiment, the first displacement mechanism is connected to the angle actuator by means of a linear actuator, where the linear actuator allows the coil to be displaced along an x axis.

In a variation of the previous alternative embodiment, the magnetic stimulation machine further comprises a second displacement mechanism connected between the first displacement mechanism and the angle actuator; where the second displacement mechanism moves the coil along a y axis.

A variation of the previous alternative embodiment, the magnetic stimulation machine further comprises a second displacement mechanism connected between the first displacement mechanism and the angle actuator and a linear actuator connected between the angle actuator and the second displacement mechanism, where the second displacement mechanism moves the coil along a y axis, and the linear actuator allows the coil to be displaced along an x axis.

A variation of the previous alternative embodiment, the magnetic stimulation machine further comprises a third displacement mechanism connected between the angle actuator and the linear actuator, the third displacement mechanism is connected to a distal end of a shaft of the linear actuator, the third displacement mechanism has: a first curved guide connected to the stem, a third carriage movably connected to the first curved guide, and a third drive mechanism connected to the third carriage, where the third displacement mechanism moves the coil in a first path, and the third drive mechanism moves the third carriage along the first curved guide.

A variation of the previous alternative embodiment, the magnetic stimulation machine further comprises a fourth displacement mechanism connected between the linear actuator and the second displacement mechanism; the fourth displacement mechanism has: a second curved guide connected to the second displacement mechanism, a fourth carriage movably connected to the second curved guide, and a fourth drive mechanism connected to the fourth carriage, where the fourth displacement mechanism moves the coil in a second path, and the fourth drive moves the fourth carriage along the second curved guide.

A variation of the previous alternative embodiment, the magnetic stimulation machine further comprises a rotating platform located on the surface, where the body is arranged on the rotating platform.

On the other hand, the present document also discloses methods for the magnetic stimulation of tissues of a body.

In general, in the magnetic stimulation of tissues that this document discloses, the path of the magnetic field on the tissue following different trajectories in a three-dimensional space with respect to a body containing a tissue, as a function of time based on a determined movement pattern and a generation of magnetic field in accordance with an activation signal.

One of the methods for the magnetic stimulation of tissues of a body, comprising the following steps: a) placing a coil operatively on a tissue of a body; b) generating a magnetic field by means of the coil; and c) moving the coil according to a determined movement pattern around the tissue to stimulate it.

In a particular embodiment of the method, in step b), the magnetic field obeys an activation signal.

In another particular embodiment of the method, in step c), the movement pattern follows a path along a longitudinal axis of the tissue.

In a specific embodiment of the method, in step b) the magnetic field generated on the tissue has an intensity between 0.1 mT (milliteslas) and 200 mT (milliteslas).

Optionally, in step c), the movement pattern changes the orientation of the coil.

Alternatively, in step c) the movement pattern performs the following sub-steps i) moving the coil following a movement pattern in a direction parallel to a longitudinal axis of the tissue until the position of the coil exceeds the length of the tissue of the body and ii) changing the orientation of the coil such that the axis of the coil forms a 90 degree angle with the longitudinal axis of the tissue.

In a specific embodiment of the method for the magnetic stimulation of tissues of a body, sub-step ii) corresponds to removing the electrical supply from the coil.

In another particular embodiment of the method for the magnetic stimulation of body tissues, after sub-step ii) there follows a sub-step iii) in which the coil is moved following a second movement pattern in which the angle is conserved 90 degrees from the axis of the coil to the longitudinal axis of the tissue and gradually move the coil of tissue away until the magnetic field no longer stimulates the tissue.

In another particular embodiment of the method for the magnetic stimulation of body tissues, after sub-step iii) a sub-step iv) follows in which the orientation of the coil is changed so that the axis of the coil and the longitudinal axis of the tissue are parallel.

DETAILED DESCRIPTION

The present disclosure relates to a machine and method for magnetic tissue stimulation. This method uses a magnetic field that follows a pattern of movement in three-dimensional space with respect to a tissue.

The approach to magnetic stimulation of tissue of the present disclosure comprises the path of the magnetic field that varies as a function of time on the tissue. The magnetic field follows the trajectories of the magnetic field generating coil based on a determined movement pattern of said coil and a magnetic field generation based on a stimulation pattern and thus distribute the field energy throughout the body, stimulating the tissue.

Particularly the disclosed magnetic stimulation applies to biological tissues, which will be described later in this document.

Figure 1:
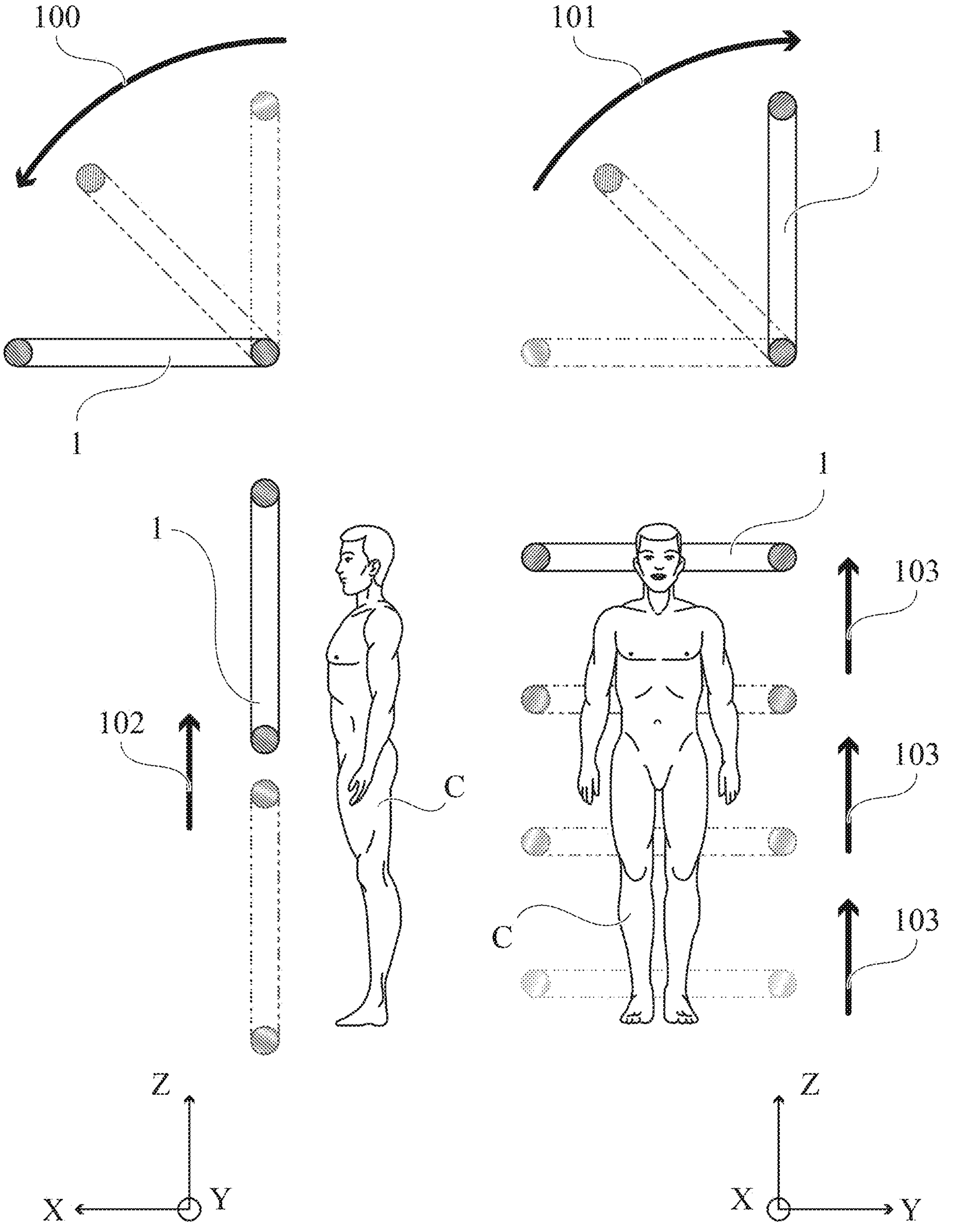
FIG. 1 shows an example of the directions of travel and twists in two degrees of freedom that the present disclosure allows.

Referring to FIG. 1, in one example, the magnetic stimulation using the present disclosure is based on the movement of a magnetic field in a living tissue, of a body (C). Said movement can be performed in two ways, the first way is by using the machine of the present disclosure that executes the method of the present disclosure, the second way is that an operator executes the steps of the method of the present disclosure. The method of disclosure will be described later in this document.

For its part, the machine of the present disclosure moves a coil (1) in different directions of a rectilinear or circular path with respect to the longitudinal axis of a body (C). For example, the machine can move the coil (1) in a Cartesian coordinate system with x, y, z axes, where the x axis corresponds to a longitudinal direction, the y axis corresponds to a transverse direction of a body (C), and the z axis corresponds to a vertical direction of the body (C).

The machine makes it possible to rotate the coil (1) with a first path (100) or with a second path (101) that changes the angle between the axis of the coil (1) and the longitudinal axis of the tissue. In this way, the vector of the magnetic field is drastically changed, establishing an electromagnetic dipole organization at the tissue cellular level and at the intracellular level.

For the understanding of the present disclosure, it should be understood that electromagnetic dipole rearrangement is the electromagnetic orientation of the cells constituting a tissue at the cellular level and at the intracellular level.

The cells that make up the tissue are considered an electromagnetic dipole, which in turn is a point element that produces a dipole electromagnetic field that interacts with the magnetic field supplied with the disclosed machine. By moving the magnetic field in the three-dimensional space around the body that contains a tissue, the electromagnetic orientation changes at the cellular level and at the intracellular level.

Optionally, the machine of the disclosure moves the coil (1) keeping its axis perpendicular to the longitudinal axis of the body tissue (C) following a third path (102) along the z axis.

Alternatively, in the same example, after carrying out the third path (102), the machine rotates the coil (1) in the first path (100), changing the angle between the axis of the coil (1) and the axis longitudinal tissue. In this way, the vector of the magnetic field is drastically changed, establishing an electromagnetic dipole organization at the tissue cellular level and at the intracellular level.

In another particular example of the machine of the present disclosure, the coil (1) moves while maintaining its axis coaxial to the longitudinal axis of the body tissue (C) following a fourth path (103) along the z axis.

Optionally, in the same previous example, after carrying out the third path (102), the machine rotates the coil (1) in the second path (101), changing the angle between the axis of the coil (1) and the longitudinal axis of the tissue. In this way, an electromagnetic dipole organization is established at the cellular level of the tissue and at the intracellular level.

Optionally, the direction of the path followed by the coil of the machine of the present disclosure depends on the geometry of the body (C) and said path follows the length of said body (C).

Length will be understood herein as the longest dimension of said flat-shaped body or of a three-dimensional body; in general, it is notably greater with respect to the other dimensions of the same.

The machine of the present disclosure can move the coil (1) with respect to a z axis, so that a path is generated with the magnetic field on a body (C). Preferably, the body (C) is a living being, such as a human or an animal, or it can be a part of said living being, such as a hand, arm, leg, head, torso, etc., said part of said living being contains a tissue or group of tissues.

On the other hand, the coil (1) is a device to which an electric current is supplied by an electric power source and generates a magnetic field. Preferably, the magnetic field extends from the inside of the coil (1) towards the outside thereof in a direction predetermined by the geometry of the coil (1) and the direction of the current flowing through the coil (1). For example, the coil (1) can be circular, toroidal, elliptical, oblong, triangular, square, rectangular, pentagonal, hexagonal, octagonal, or polygonal with more than three sides.

For the understanding of this document, the electrical energy source is a device capable of maintaining an electrical potential difference between two or more terminals such as an alternating current source, direct current source, batteries, photovoltaic source, thermoelectric source, among others devices capable of maintaining a difference in electrical potential or voltage between two or more terminals known to a person of ordinary skill in the art or combinations. The source of electrical energy allows the supply of the electrical power required for the operation of the coil (1).

In the present disclosure it should be understood that a movement pattern refers to sequentially organized movements that follow a determined trajectory with respect to a body, said movement pattern can be expressed by an equation, an algorithm or a combination of both. In a particular example, said movement pattern involves stopping the movement at a specific position on the trajectory and continuing after this stop.

Optionally, in a particular example of the present disclosure, an electrical power source supplies the electrical power required by the electrical elements of the magnetic tissue stimulation machine.

In a particular example of the present disclosure, the operating voltage of the coil (1) has a voltage value between approximately (approx.) 330 V and approx. 20 kV, and generates a magnetic field in the body between approx. 0.1 mT (milliteslas) equivalent to 1 Gauss, and approx. 200 mT, equivalent to 2000 Gauss, and preferably between approx. 40 mT and approx. 200 mT.

The magnetic field that is applied to the body by the disclosed machine is between approx. 0.1 mT and approx. 200 mT, and preferably between approx. 40 mT and approx. 200 mT.

Optionally, the operating voltage of the coil (1) has a voltage value between approx. 0.33 kV and approx. 20 kV, between approx. 0.83 kV and approx. 19.5 kV, between approx. 1.33 kV and approx. 19 kV, between approx. 1.83 kV and approx. 18.5 kV, between approx. 2.33 kV and approx. 18 kV, between approx. 2.83 kV and approx. 17.5 kV, between approx. 3.33 kV and approx. 17 kV, between approx. 3.83 kV and approx. 16.5 kV, between approx. 4.33 kV and approx. 16 kV, between approx. 4.83 kV and approx. 15.5 kV, between approx. 5.33 kV and approx. 15 kV, between approx. 5.83 kV and approx. 14.5 kV, between approx. 6.33 kV and approx. 14 kV, between approx. 6.83 kV and approx. 13.5 kV, between approx. 7.33 kV and approx. 13 kV, between approx. 7.83 KV and approx. 12.5 kV, between approx. 8.33 kV and approx. 12 kV, between approx. 8.83 kV and approx. 11.5 kV, between approx. 9.33 kV and approx. 11 KV, between approx. 9.83 kV and approx. 10.5 kV, between approx. 1.33 kV and approx. 20 kV, between approx. 2.33 kV and approx. 20 kV, between approx. 3.33 kV and approx. 20 kV, between approx. 4.33 kV and approx. 20 kV, between approx. 5.33 kV and approx. KV, between approx. 6.33 kV and approx. 20 kV, between approx. 7.33 kV and approx. kV, between approx. 8.33 kV and approx. 20 kV, between approx. 9.33 kV and approx. kV, between approx. 10.33 kV and approx. 20 kV, between approx. 11.33 kV and approx. 20 kV, between approx. 12.33 kV and approx. 20 kV, between approx. 13.33 kV and approx. 20 kV, between approx. 14.33 kV and approx. 20 kV, between approx. 15.33 KV and approx. 20 kV, between approx. 16.33 kV and approx. 20 kV, between approx. 17.33 kV and approx. 20 kV, between approx. 18.33 kV and approx. 20 kV, between approx. 19.33 kV and approx. 20 KV, between approx. 0.33 kV and approx. 19 kV, between approx. 0.33 kV and approx. 18 kV, between approx. 0.33 kV and approx. 17 kV, between approx. 0.33 kV and approx. 16 kV, between approx. 0.33 kV and approx. kV, between approx. 0.33 kV and approx. 14 kV, between approx. 0.33 kV and approx. 13 kV, between approx. 0.33 kV and approx. 12 kV, between approx. 0.33 kV and approx. 11 kV, between approx. 0.33 kV and approx. 10 kV, between approx. 0.33 kV and approx. 9 kV, between approx. 0.33 kV and approx. 8 kV, between approx. 0.33 kV and approx. 7 kV, between approx. 0.33 kV and approx. 6 kV, between approx. 0.33 kV and approx. kV, between approx. 0.33 kV and approx. 4 kV, between approx. 0.33 kV and approx. 3 kV, between approx. 0.33 kV and approx. 2 kV, between approx. 0.33 kV and approx. 1 kV, between approx. 1.33 kV and approx. 2.33 kV, between approx. 2.33 kV and approx. 3.33 kV, between approx. 3.33 kV and approx. 4.33 kV, between approx. 4.33 kV and approx. 5.33 kV, between approx. 5.33 kV and approx. 6.33 kV, between approx. 6.33 kV and approx. 7.33 kV, between approx. 7.33 kV and approx. 8.33 kV, between approx. 8.33 kV and approx. 9.33 kV, between approx. 9.33 kV and approx. 10.33 kV, between approx. 10.33 kV and approx. 11.33 kV, between approx. 11.33 kV and approx. 12.33 kV, between approx. 12.33 kV and approx. 13.33 kV, between approx. 13.33 kV and approx. 14.33 kV, between approx. 14.33 kV and approx. 15.33 kV, between approx. 15.33 kV and approx. 16.33 kV, between approx. 16.33 kV and approx. 17.33 kV, between approx. 17.33 kV and approx. 18.33 kV, between approx. 18.33 kV and approx. 19.33 kV, between approx. 19.33 kV and approx. 20 kV.

Alternatively, the magnetic field intensity generated by the disclosed machine is selected in the range of approx. 1 mT and approx. 10 mT, between approx. 10 mT and approx. 20 mT, between approx. 20 mT and approx. 30 mT, between approx. 30 mT and approx. 40 mT, between approx. 40 mT and approx. 50 mT, between approx. 50 mT and approx. 60 mT, between approx. 60 mT and approx. 70 mT, between approx. 70 mT and approx. 80 mT, between approx. 80 mT and approx. 90 mT, between approx. 90 mT and approx. 100 mT, between approx. 100 mT and approx. 110 mT, between approx. 110 mT and approx. 120 mT, between approx. 120 mT and approx. 130 mT, between approx. 130 mT and approx. 140 mT, between approx. 140 mT and approx. 150 mT, between approx. 150 mT and approx. 160 mT, between approx. 160 mT and approx. 170 mT, between approx. 170 mT and approx. 180 mT, between approx. 180 mT and approx. 190 mT, between approx. 190 mT and approx. 200 mT, between approx. 1 mT and approx. 10 mT, between approx. 1 mT and approx. 20 mT, between approx. 1 mT and approx. 30 mT, between approx. 1 mT and approx. 40 mT, between approx. 1 mT and approx. 50 mT, between approx. 1 mT and approx. 60 mT, between approx. 1 mT and approx. 70 mT, between approx. 1 mT and approx. 80 mT, between approx. 1 mT and approx. 90 mT, between approx. 1 mT and approx. 100 mT, between approx. 1 mT and approx. 110 mT, between approx. 1 mT and approx. 120 mT, between approx. 1 mT and approx. 130 mT, between approx. 1 mT and approx. 140 mT, between approx. 1 mT and approx. 150 mT, between approx. 1 mT and approx. 160 mT, between approx. 1 mT and approx. 170 mT, between approx. 1 mT and approx. 180 mT, between approx. 1 mT and approx. 190 mT, between approx. 1 mT and approx. 200 mT, between approx. 1 mT and approx. 200 mT, between approx. 200 mT and approx. 190 mT, between approx. 190 mT and approx. 180 mT, between approx. 180 mT and approx. 170 mT, between approx. 170 mT and approx. 160 mT, between approx. 160 mT and approx. 150 mT, between approx. 150 mT and approx. 140 mT, between approx. 140 mT and approx. 130 mT, between approx. 130 mT and approx. 120 mT, between approx. 120 mT and approx. 110 mT, between approx. 110 mT and approx. 100 mT, between approx. 100 mT and approx. 90 mT, between approx. 90 mT and approx. 80 mT, between approx. 80 mT and approx. 70 mT, between approx. 70 mT and approx. 60 mT, between approx. 60 mT and approx. 50 mT, between approx. 50 mT and approx. 40 mT, between approx. 40 mT and approx. 30 mT, between approx. 30 mT and approx. 20 mT, between approx. 20 mT and approx. 10 mT. 70 mT and approx. 60 mT, between approx. 60 mT and approx. 50 mT, between approx. 50 mT and approx. 40 mT, between approx. 40 mT and approx. 30 mT, between approx. 30 mT and approx. 20 mT, between approx. 20 mT and approx. 10 mT. 70 mT and approx. 60 mT, between approx. 60 mT and approx. 50 mT, between approx. 50 mT and approx. 40 mT, between approx. 40 mT and approx. 30 mT, between approx. 30 mT and approx. 20 mT, between approx. 20 mT and approx. 10 mT.

As used herein, "approximately" or "approx." refers to a variation of ±20% of the value of the mentioned variable, for example, a variation of 20% of the electric field intensity, or a variation of 20% of the operating voltage of the coil or of an oscillation frequency from the alternating current source.

In an example of the disclosure machine, the coil (1) is a Helmholtz coil. One of the advantages of this type of coil (1) is that it allows a homogeneous magnetic field to be generated in a particular region of the body to be stimulated.

Alternatively, in another example of the machine of the present disclosure, the coil (1) is an array of coils. The coil array can be a unitary array with a single coil or have more than one coil.

Optionally, in another example of the machine of the present disclosure, coil (1) is a Helmholtz coil array. The Helmholtz coil arrangement can also be a unitary arrangement with a single Helmholtz coil of coils or have more than one Helmholtz coil.

In another embodiment of the machine of the disclosure the coil (1) is a loop of wire through which alternating electric current or a direct electric current circulates. Optionally, the coil (1) is a set of turns that make up an air core solenoid. In a particular example of the present disclosure the coil (1) is an air core solenoid.

Also, in one embodiment of the disclosure, the coil (1) has a core that is made of a material that is selected from among others air, ferrite, iron, iron powder, nickel, iron and molybdenum alloy cores, iron, silicon and aluminum alloy, iron and silicon alloy cores, cores made of sheets or plates, ferrite powders, cores formed by binding of powder with resins among other cores known to a person of moderate skill in the matter. Alternatively, different combinations of materials are used for the core in order to achieve changes over the hysteresis of the core itself.

Optionally, the form of construction of the core of the coil (1) can be by means of sheets of the material, compacted granules, pellets of different geometric shapes in three dimensions such as polyhedra with flat faces (e.g. pyramidal, cubic, prismatic, among others) or geometric shapes with curved surfaces such as (eg cylindrical, conical, spherical, among others).

In another example of the present disclosure, coil (1) is an array of coils that is operatively connected to a control circuit.

In another particular example of the machine of the present document, the coil (1) is an arrangement of N coils, where N is a natural number between 1 and 200.

The control circuit comprises a computing unit, an electrical power source connected to the computing unit, a decoupling circuit connected to the electrical power source and the computing unit, the coil array connected to the computing unit and the decoupling circuit; The computing unit implements the method of the disclosure (magnetic tissue stimulation method) and is configured with the control circuit to generate the stimulation signals that are sent from the computing unit, transmitted through the decoupling circuit and receives the arrangement of coils that generate magnetic fields to stimulate living tissues. In this way, the computing unit of the control circuit allows to control the activation of the coil (1) in order to change the intensity of the magnetic field to stimulate the body tissue (C).

In one embodiment of the machine of the present disclosure, the computing unit is selected from the group comprising programmable logic controllers (PLC), microprocessors, DSCs (Digital Signal Controller), FPGAs (Field Programmable Gate Array), CPLDs (Complex Programmable Logic Device), ASICs (Application Specific Integrated Circuit), SoCs (System on Chip), PsoCs (Programmable System on Chip), computers, servers, tablets, cell phones, smart phones, signal generators and equivalent control units known to a person of moderate skill in the field and combinations of these.

On the other hand, the decoupling circuit allows to electrically decouple the source of electrical energy from the coil arrangement, said circuit can be based on optocouplers, relays, operational amplifiers, resistors, capacitors, transformers, diodes, thyristors, power transistors, BJT, FETs, IGBTs, TRIACs, DIACs, SCRs, electronic switching devices, combinations of these and other electronic elements to electrically decouple two circuits or electrical elements.

In another embodiment of the machine of the present disclosure, the computing unit allows, in addition to controlling the activation of the coil (1), to control the movement of the coil (1).

In an optional embodiment of the present disclosure, the control circuit has a second computing unit in charge of controlling the movement of the machine of the present disclosure while a first computing unit controls the activation of the coil (1).

In general, a computing unit can control the movement of the magnetic stimulation machine of the present disclosure by activating the motor mechanisms that the machine has and in turn dosing the supply of energy that comes from an electrical energy source and that is delivered to the coil (1).

In a particular example of the disclosure, the coil (1) is directly connected to a source of alternating current with a voltage between approximately 330 Vac (volts in alternating current) to approximately 20 kVac (kilovolts in alternating current) at frequencies between approximately 0, 1 Hz and approximately 50 KHz.

Alternatively, the oscillation frequency of the alternating current source is in a frequency range that is selected from approx. 0.1 Hz and approx. 1 Hz, between approx. 0.3 Hz and approx. 0.8 Hz, between approx. 0.5 Hz and approx. 0.6 Hz, between approx. 0.7 Hz and approx. 0.4 Hz, between approx. 0.9 Hz and approx. 0.2 Hz, between approx. 0.3 Hz and approx. 1 Hz, between approx. 0.5 Hz and approx. 1 Hz, between approx. 0.7 Hz and approx. 1 Hz, between approx. 0.9 Hz and approx. 1 Hz, between approx. 0.1 Hz and approx. 0.8 Hz, between approx. 0.1 Hz and approx. 0.6 Hz, between approx. 0.1 Hz and approx. 0.4 Hz, between approx. 0.1 Hz and approx. 0.2 Hz, between approx. 0.3 Hz and approx. 0.5 Hz, between approx. 0.5 Hz and approx. 0.7 Hz, between approx. 0.7 Hz and approx. 0.9 Hz, between approx. 0.1 Hz and approx. 1000 Hz, between approx. 100 Hz and approx. 900 Hz, between approx. 200 Hz and approx. 800 Hz, between approx. 300 Hz and approx. 700 Hz, between approx. 400 Hz and approx. 600 Hz, between approx. 500 Hz and approx. 500 Hz, between approx. 600 Hz and approx. 400 Hz, between approx. 700 Hz and approx. 300 Hz, between approx. 800 Hz and approx. 200 Hz, between approx. 900 Hz and approx. 100 Hz, between approx. 1000 Hz and approx. 0.1 Hz, between approx. 100

Hz and approx. 1000 Hz, between approx. 200 Hz and approx. 1000 Hz, between approx. 300 Hz and approx. 1000 Hz, between approx. 400 Hz and approx. 1000 Hz, between approx. 500 Hz and approx. 1000 Hz, between approx. 600 Hz and approx. 1000 Hz, between approx. 700 Hz and approx. 1000 Hz, between approx. 800 Hz and approx. 1000 Hz, between approx. 900 Hz and approx. 1000 Hz, between approx. 0.1 Hz and approx. 900 Hz, between approx. 0.1 Hz and approx. 800 Hz, between approx. 0.1 Hz and approx. 700 Hz, between approx. 0.1 Hz and approx. 600 Hz, between approx. 0.1 Hz and approx. 500 Hz, between approx. 0.1 Hz and approx. 400 Hz, between approx. 0.1 Hz and approx. 300 Hz, between approx. 0.1 Hz and approx. 200 Hz, between approx. 0.1 Hz and approx. 100 Hz, between approx. 100 Hz and approx. 200 Hz, between approx. 200 Hz and approx. 300 Hz, between approx. 300 Hz and approx. 400 Hz, between approx. 400 Hz and approx. 500 Hz, between approx. 500 Hz and approx. 600 Hz, between approx. 600 Hz and approx. 700 Hz, between approx. 700 Hz and approx. 800 Hz, between approx. 800 Hz and approx. 900 Hz, between approx. 900 Hz and approx. 1000 Hz, between approx. 1 KHz and approx. 50 kHz, between approx. 1 Hz and approx. 50 kHz, between approx. 900 Hz and approx. 1000 Hz, between approx. 1 KHz and approx. 50 kHz, between approx. 1 Hz and approx. 50 KHz, between approx. 900 Hz and approx. 1000 Hz, between approx. 1 kHz and approx. 50 kHz, between approx. 1 Hz and approx. 50 KHz.

In another particular example, the coil is connected to an alternating current source of 120 Vac at 60 Hz, in another example, the coil (1) is connected to a source of alternating current of 120 Vac at 50 Hz, in another example, the Coil (1) is connected to a 220 Vac at 60 Hz alternating current source, in another example, the coil (1) is connected to a 220 Vac at 50 Hz alternating current source. However, the coil (1) can operate in direct current based on a pattern established or not in a computer unit.

For the understanding of the present disclosure, the term Vac refers to alternating current electric voltage or potential. In the same way, the term "tissue" refers to the biological tissues of living beings made up of one or more cells, it can be made up of cells of a single class, all the same, or of several types of cells arranged in an orderly manner forming an organ, or organism, or by a group of organs or group of organisms. The mentioned tissue can be healthy tissue such as epithelial tissue, connective tissue, muscle tissue, nervous tissue, or combinations of these. The tissue can also be a tissue with a total or partial biochemical imbalance in healthy tissue, said biochemical imbalance in turn may correspond to benign neoplastic tissue, malignant neoplastic tissue or any cell out of homeostasis or in homeostasis. In addition, tissue can refer to cells in vivo or prior to implanting said cells in an in vivo environment.

Optionally, the tissue can come from or be from animals including, without limitation; mammals, bird species, including chickens, turkeys, geese, and ducks; fish, crustacean species (shrimp, lobster, crayfish); and reptiles like crocodiles and alligators. The term "mammal", as used herein, refers to any mammal classified as a mammal, including humans, non-human primates, such as cynomolgus monkeys, chimpanzees, baboons, and gorillas; domestic and farm animals including equine species, bovine species, swine species, goat species, canine species, feline species, sheep species, rabbits, llamas; ungulates, such as cattle, sheep, pigs, horses, goats; canine, feline, murine, rabbit; and rodents such as guinea pigs, hamsters, and rats.

Alternatively, the tissue is plant tissue and can be derived from or from plants that broadly include all plants, herbs, and lower plants, such as fungi and algae.

The stimulation of a biological tissue refers to administering a magnetic field to said biological tissue to induce certain changes in the characteristics of said biological tissue, such as the impedance response of the tissue, the vascularization of the tissue, the temperature of the tissue, the health of the tissue, tissue growth rate, among others.

Figure 2:
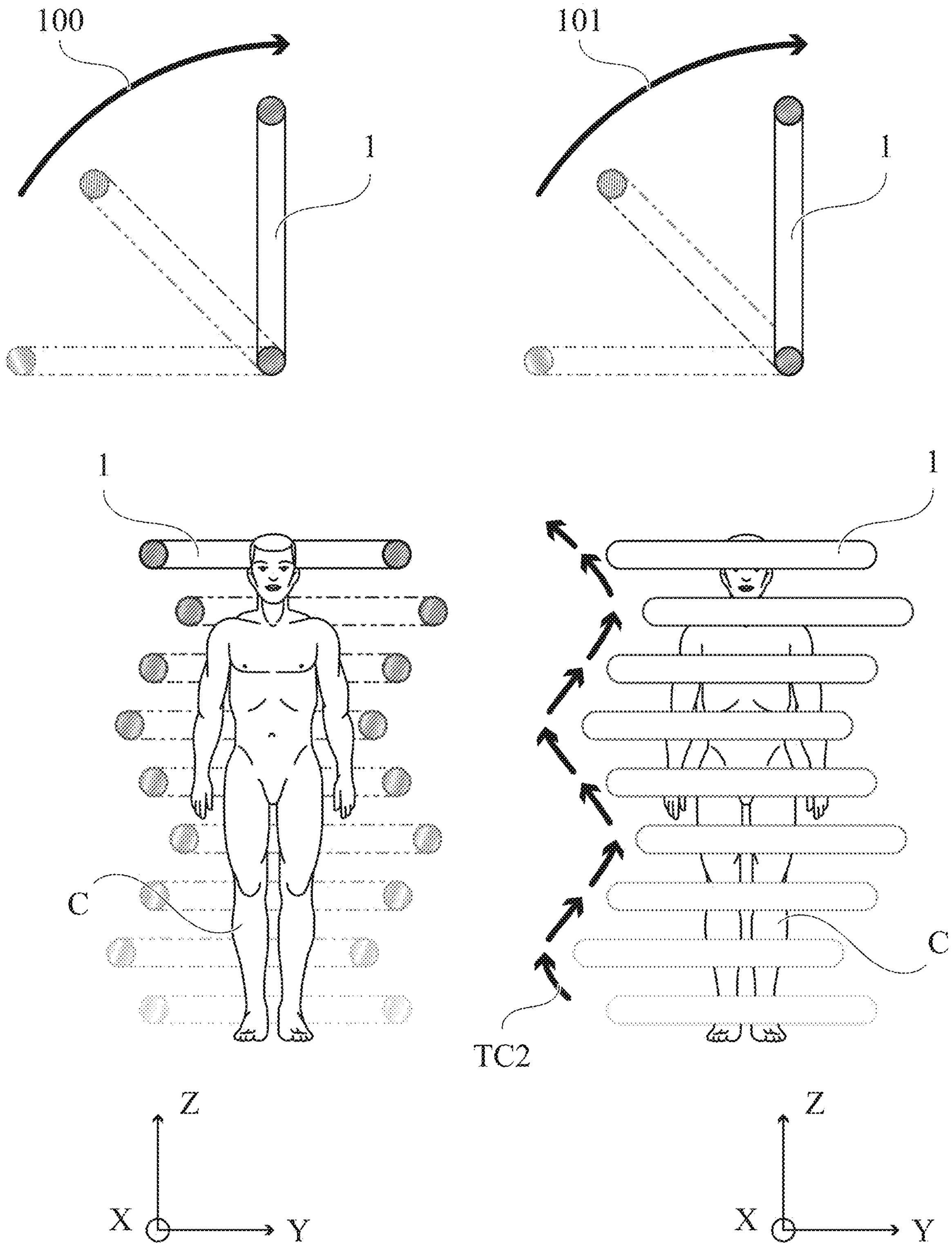
FIG. 2 shows an example of the directions of travel and three-degree rotations that the present disclosure allows.

Referring to FIG. 2, in an example of the present disclosure, with the help of the machine and the method of the present disclosure, a travel of the coil (1) is made on an axis parallel to the longitudinal axis of a body (C) which in this example particular is a tissue in a human body.

In the example, the path of the coil (1) follows a movement pattern in the second predetermined path (TC2) in which the magnetic field is parallel to the longitudinal axis of the body (C) throughout the entire path and at the end of this path, the orientation of the coil (1) with respect to the body (C) is changed following the first path (100).

In a particular example, the second predetermined path (TC2) is zigzag, starting from the base of the body (C) until it exceeds the length of said body (C) and changes the orientation of the coil (1) with respect to the body (C) following the first path (100). In a specific embodiment, the orientation of the coil (1) can be changed using an angle actuator that rotates the coil (1).

Alternatively, the method of the present disclosure can be carried out by an operator holding the coil (1), and moving the coil (1) following a particular movement pattern to magnetically stimulate a tissue of a body (C). For example, the operator can carry out the strokes of the coil (1) that have been described.

In another example of the disclosure, the travel of the coil (1) begins in the upper part of said body (C), and ends in the lower part of said body, for example, at the feet.

For the understanding of the present disclosure, it will be understood that a zigzag trajectory corresponds to the set of points that a moving body follows in a three-dimensional or two-dimensional space in a line that alternately forms incoming and outgoing angles.

In other embodiments of the machine and method of the disclosure, the second predetermined trajectory (TC2) with respect to the body (C) is not limited to a zigzag trajectory and this is selected, among others of rectilinear trajectories (eg straight line, zigzag), curvilinear (eg circular, parabolic, elliptical, pendulum and oscillatory) or erratic trajectory based on the configuration of a movement pattern established in a computational unit. In a particular example of the magnetic stimulation machine and method, said second predetermined predetermined trajectory (TC2) comprises a movement in three-dimensional space around the body (C) and with respect to the same body (C).

Optionally in the same example, the machine rotates the coil (1) with a first path (100) or a second path (101), changing the angle between the axis of the coil (1) and the longitudinal axis of the tissue. In this way, an electromagnetic dipole organization is established at the cellular level of the tissue and at the intracellular level of the body (C).

Figure 3:
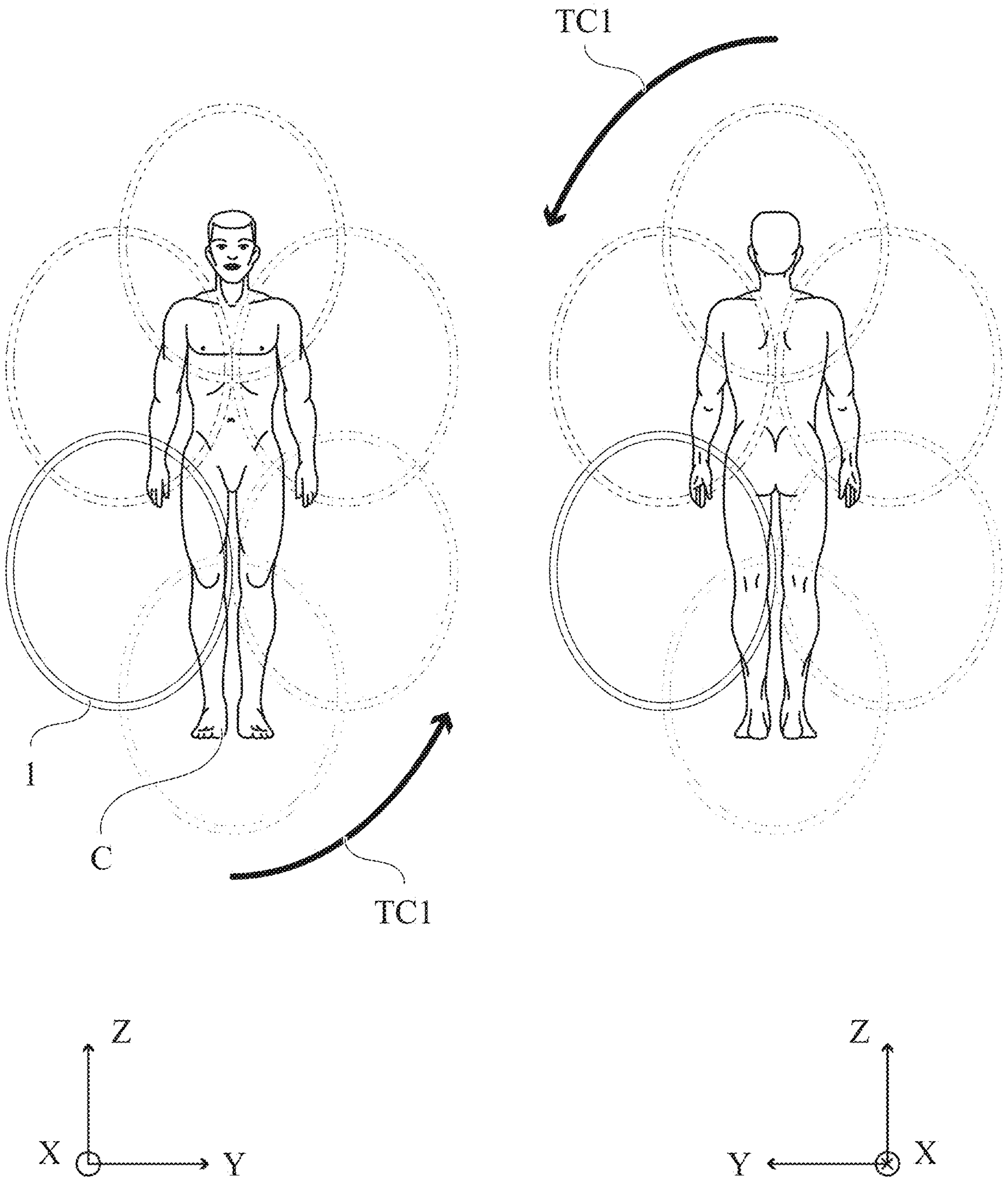
FIG. 3 shows an example a particular form of displacement allowed by the present disclosure in which the magnetic field generated by the coil is normal to the length of a subject.

Referring to FIG. 3, in another example, the method of the present disclosure allows the coil (1) to follow a first predetermined path (TC1) in which the magnetic field is perpendicular to the longitudinal axis of the body (C). The magnetic stimulation machine places the coil (1) and performs circular movements on a flat surface parallel to the axis of the body (C).

Alternatively, in an embodiment similar to the example of FIG. 3, the coil (1) follows a first predetermined trajectory (TC1) on a flat surface parallel to the axis of the body (C) and that in addition said first predetermined trajectory (TC1) is combined with a movement that is carried out in the direction towards the axis body (C) or in the opposite direction to the body (C), in such a way that the coil approaches or moves away from the body (C).

Optionally, said movement of the coil (1), of approaching or moving away from the body (C) is carried out before, during and after following the first predetermined path (TC1).

Figure 4:
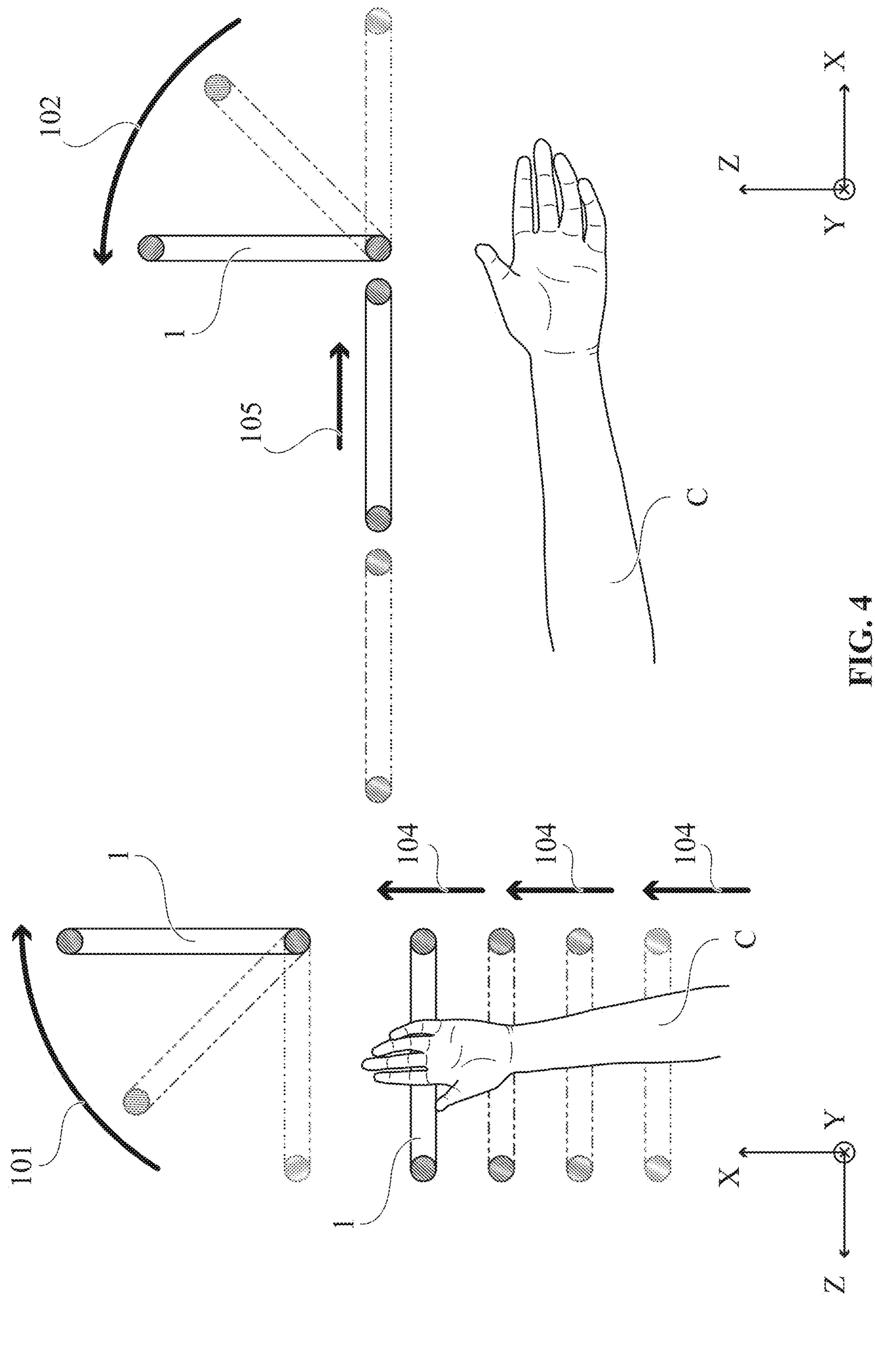
FIG. 4 shows an example of the directions of travel and twists in two degrees of freedom that the present disclosure allows for stimulating a subject's arm.

Referring to FIG. 4, similar to the example illustrated in FIG. 2, in a non-limiting example, the machine of the disclosure allows the travel of the coil (1) on the body (C), in this example, the body (C) in this specific example is a human arm or limb.

In particular FIG. 4 illustrates two examples, a first example in which said body (C) is stimulated with the coil (1) arranged in such a way that it generates a magnetic field in a longitudinal direction to the axis of the body (C) and a second example in which the direction of the magnetic field is perpendicular to the longitudinal axis of the body (C).

In the example illustrated in FIG. 4, the coil (1) of the machine of the present disclosure follows a movement pattern concentric to the longitudinal axis of the body (C) in the direction of a z-axis and following a fifth rectilinear path (104) in a first stimulation step, and In a second step the movement pattern of the coil changes the direction of the coil axis (1) forming a right angle with respect to the longitudinal axis of the body (C) according to a second path (101).

On the other hand, in the second example illustrated in FIG. 4, the axis of the coil (1) is perpendicular to the longitudinal axis of the body (C), in a first stimulation step, the movement pattern of the coil follows a sixth rectilinear trajectory (105) in the direction of the longitudinal axis of the body (C) maintaining the perpendicular direction of the axis of the coil (1) to the longitudinal axis of the body (C), and in a second step the movement pattern of the coil (1) changes the direction in such a way that said axis of the coil (1) coincides with an axis parallel to the longitudinal axis of the body (C) according to a third path (102).

Figure 5:
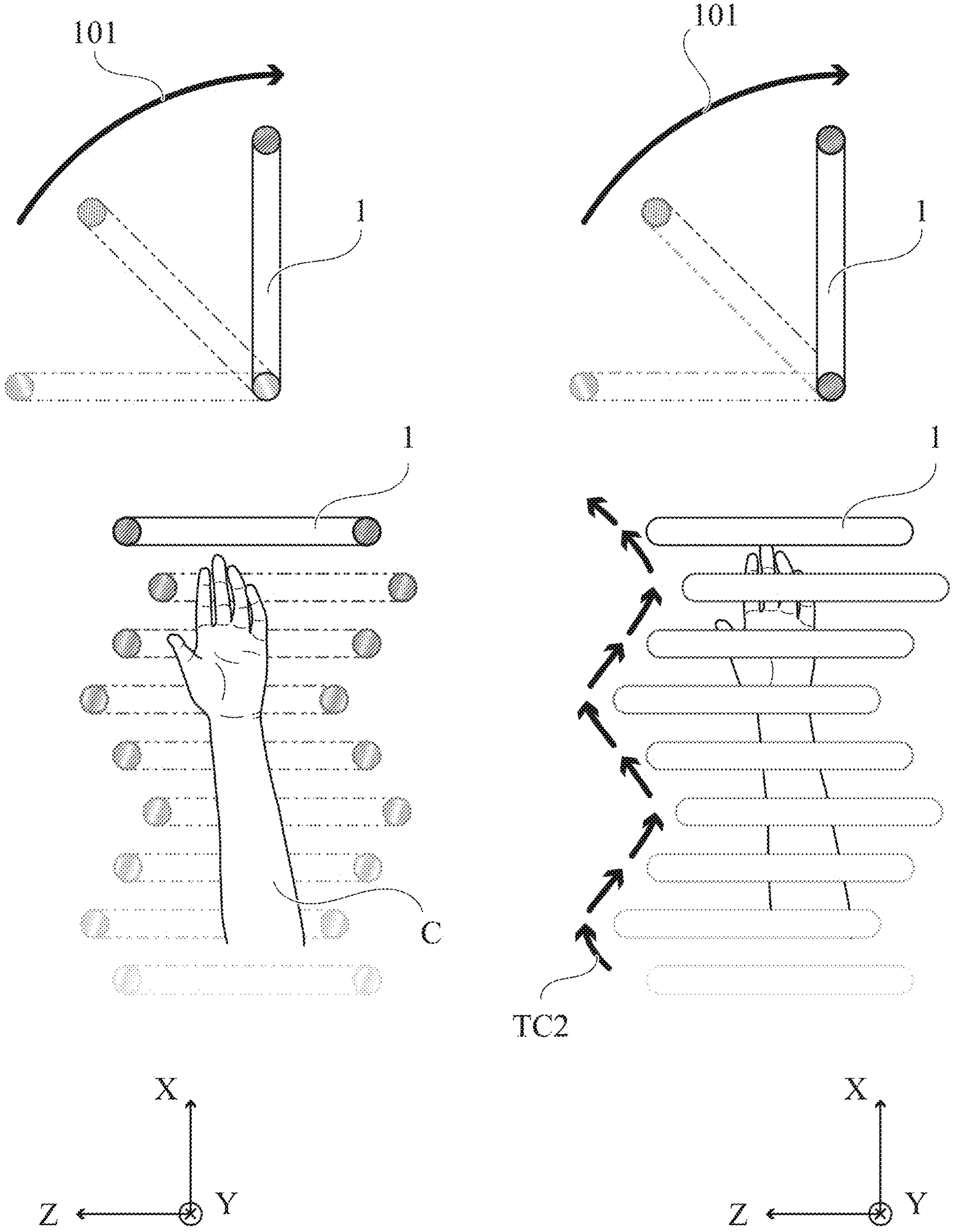
FIG. 5 shows an example of the directions of travel and rotations in three degrees of freedom that the present disclosure allows.

Referring to FIG. 5, an example is taught the same as the example of FIG. 4, but in the first stimulation step, instead of a fifth rectilinear trajectory (104) it is a second predetermined trajectory (TC2) in zigzag on a body (C), said body (C) is a human arm, in a second step the movement pattern of the coil (1) changes the direction in such a way that said coil axis (1) coincides with an axis parallel to the longitudinal axis of the body (C) according to a second trajectory (101).

Optionally, the start of the mentioned second stimulation step begins when the position of the coil (1) exceeds the length of the body (C).

In a particular example of the present disclosure, the coil (1) moves along the z axis, which extends in a direction parallel to a longitudinal axis of the body (C) that is being stimulated with the magnetic field with field magnetic. This movement is generated with the first movement mechanism (2).

Figure 6:
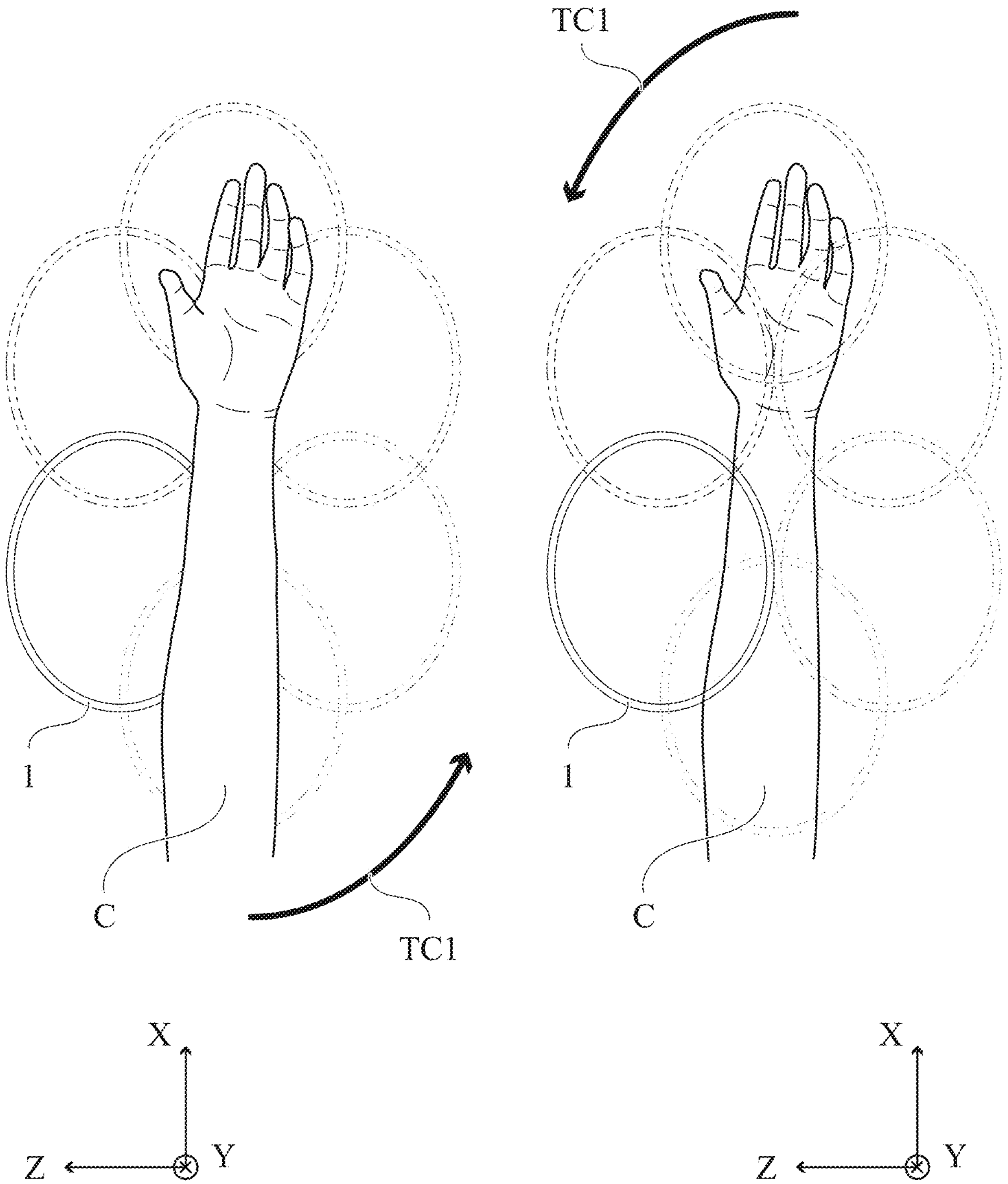
FIG. 6 shows an example a particular form of displacement allowed by the present disclosure in which the magnetic field generated by the coil is normal to the length of an arm of a subject.

Referring to FIG. 3 and FIG. 6, in this case, the machine of the present disclosure can move the coil (1) that generates the magnetic field, along a first predetermined path (TC1), with which a curved path can be generated with the magnetic field on the body (C).

Referring to FIG. 6, an example is illustrated the same as that of FIG. 3, but in which the body (C) corresponds to a human arm. Optionally, to end the tissue stimulation, the angle formed by the coil (1) with respect to the longitudinal axis of the arm can be changed. Also, the coil (1) can move towards or away from the arm when stimulated.

Optionally, said movement of the coil (1), of approaching or moving away from the arm following a specific trajectory. Said trajectory is carried out before, during or after following the first predetermined trajectory (TC1).

For example, when the angle actuator (12) arranges the coil (1) horizontally, the third displacement mechanism (11) can move the coil (1) in a first predetermined path (TC1), preferably, the first predetermined path (TC1) is closed and coil (1) moves cyclically.

The first displacement mechanism (2) is selected from the group that is selected among others from the group comprising winches, cranes, pneumatic, hydraulic, mechanical or electromechanical actuation cylinders, single-acting cylinders, double-acting cylinders, gantries provided with chain, cable, or belt hoists, where the hoists may include skids that allow movement orthogonal to the longitudinal direction, scissor lifts, trolley-guide mechanisms, and combinations thereof.

Also, the first displacement mechanism (2) can be a mechanism operated with manual force, for example, by levers, pulleys, hoists.

Figure 7:
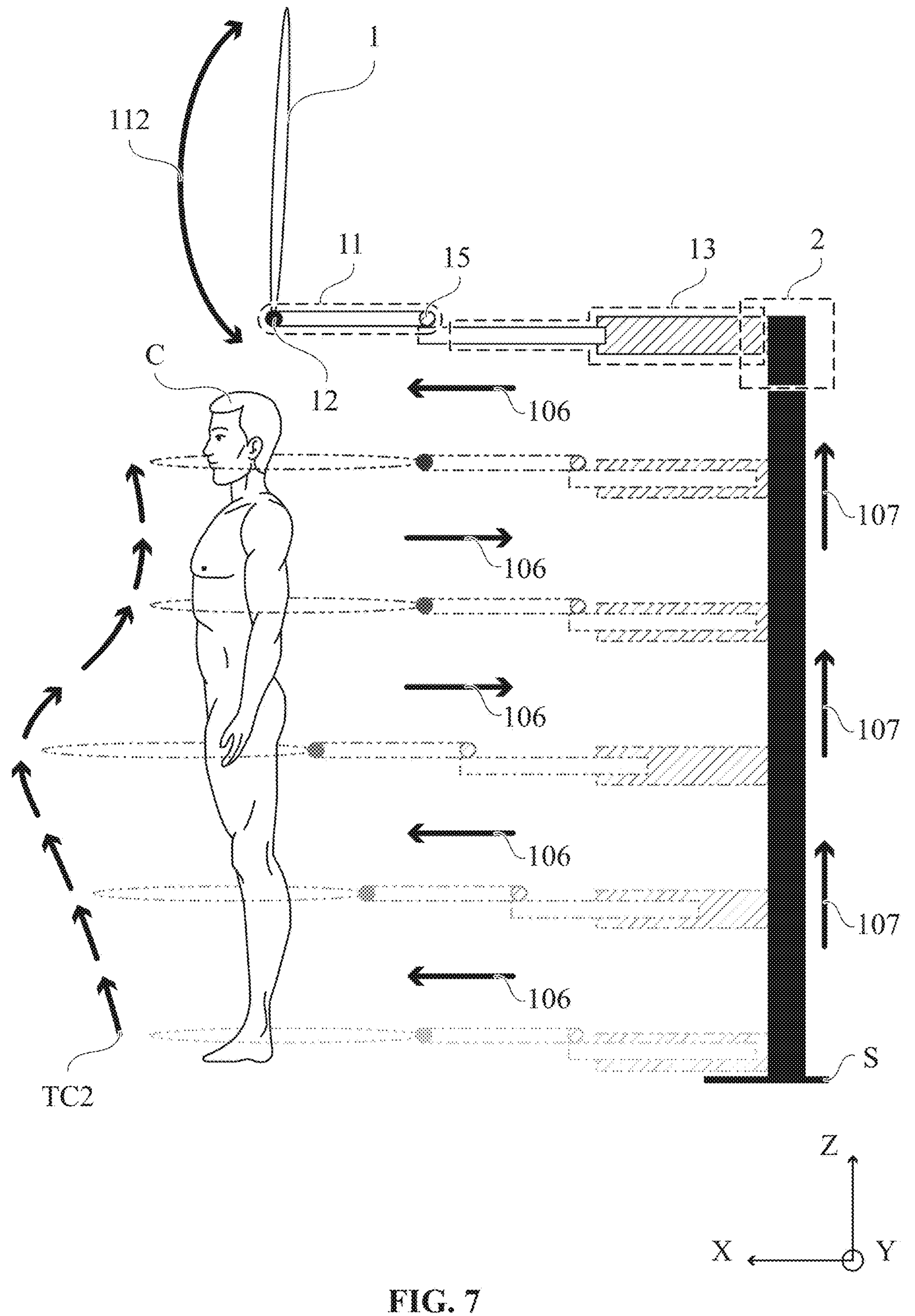
FIG. 7 shows an example a particular path of the directions of travel and twists in two degrees of freedom that the present disclosure allows along the body of a subject in a side view.
Figure 8:
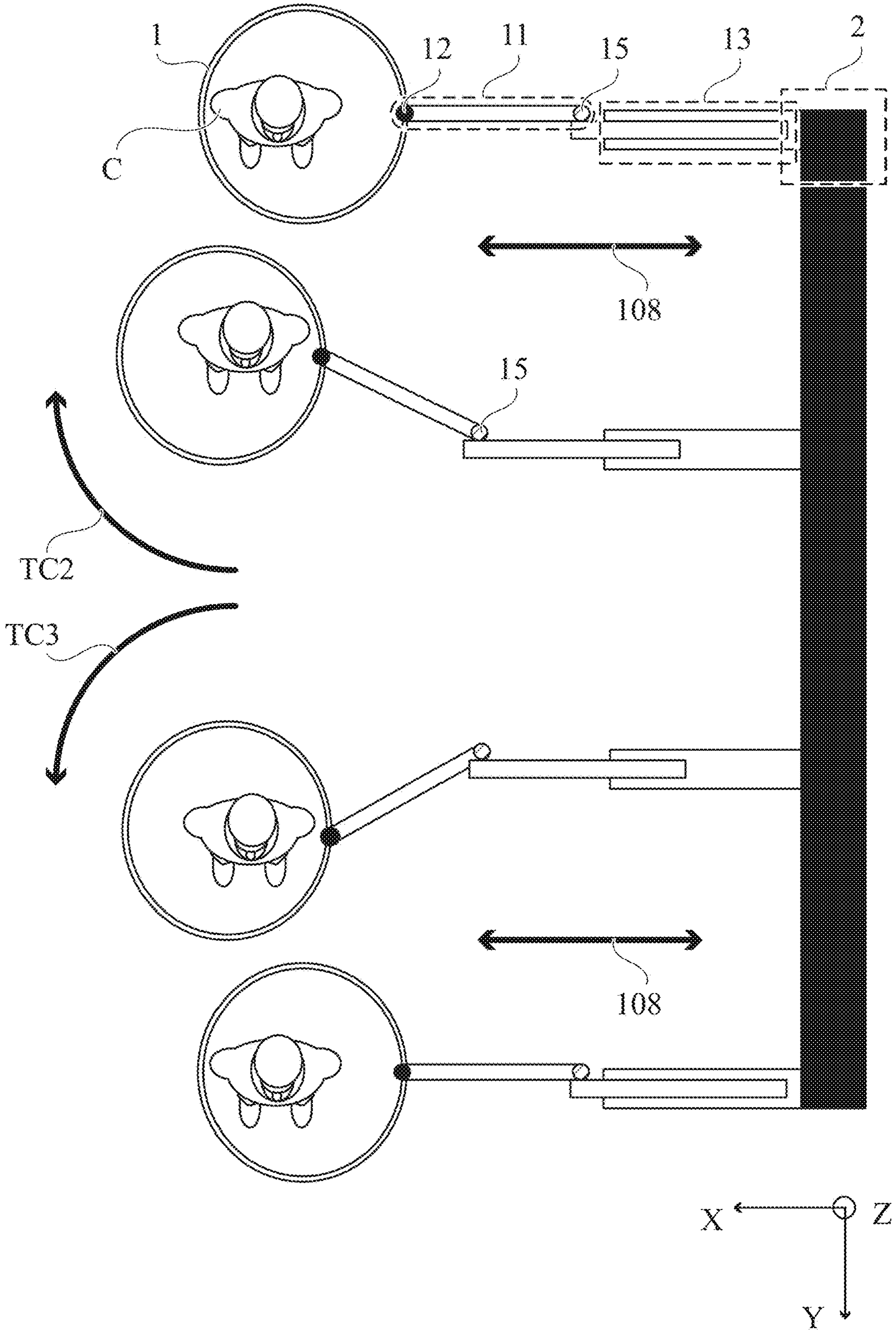
FIG. 8 shows an example a particular path of the directions of travel and twists in two degrees of freedom that the present disclosure allows along the body of a subject in a top view.
Figure 11:
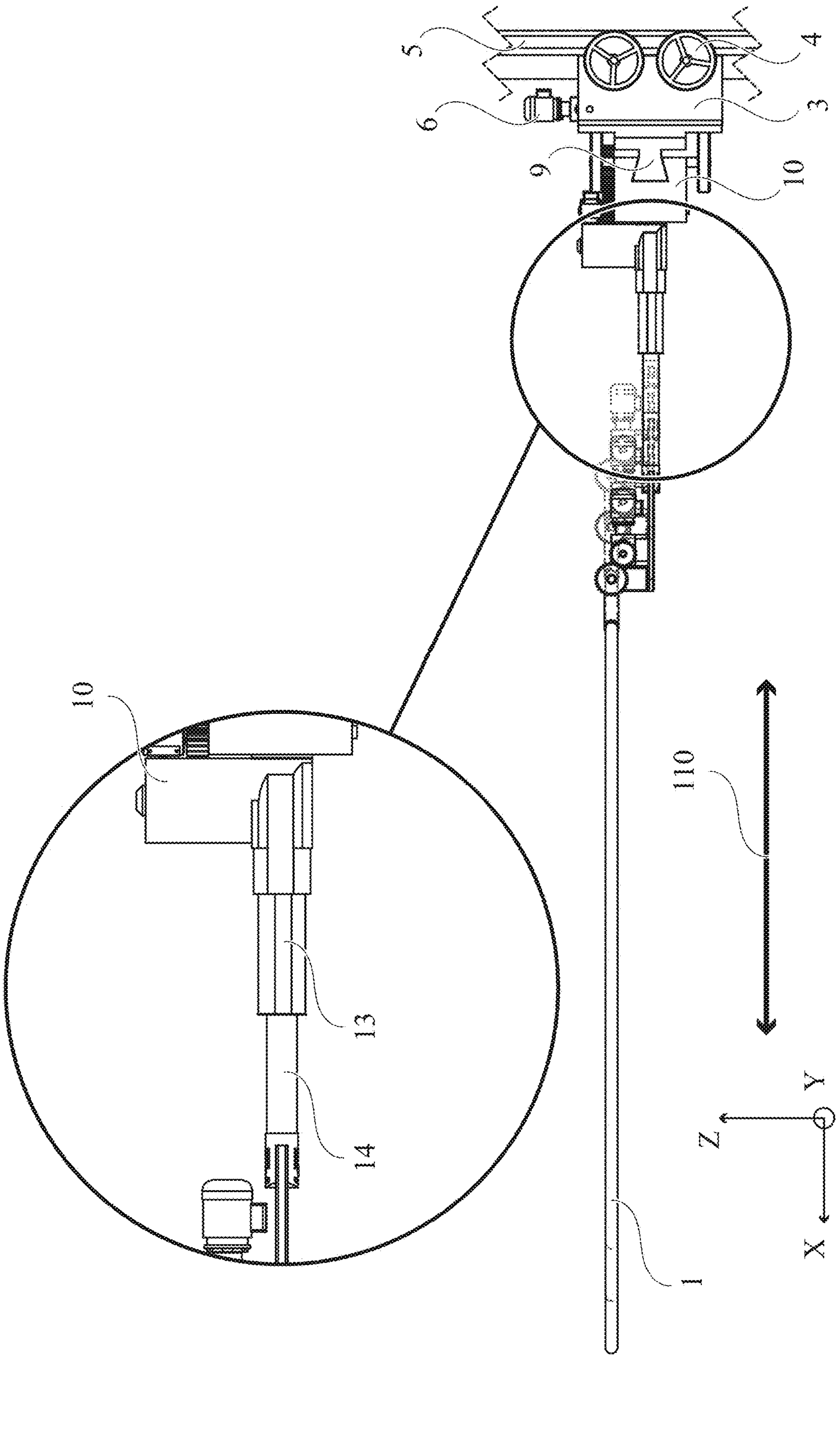
FIG. 11 shows an example of the directions of travel and twists in two degrees of freedom allowed by the present disclosure and the mechanism of movements.

Referring to FIG. 7, FIG. 8 and FIG. 11, in one embodiment of the present disclosure, the magnetic tissue stimulation machine comprises: a coil (1) that generates a magnetic field; and a first displacement mechanism (2) connected to the coil (1) and to a bearing surface (S); where the first displacement mechanism (2) moves the coil (1) around the tissue to stimulate it.

According to the above, the machine of the present disclosure can move the coil (1) along a z axis of a coordinate system in three dimensions with respect to a body containing a tissue; in some embodiments, the z-axis of the coordinate system coincides with the longitudinal axis of the body (C).

Optionally, the first displacement mechanism (2) moves the coil (1) along a z-axis of a coordinate system in three dimensions; and where the magnetic field stimulates a body (C).

Optionally, the machine of the present disclosure allows a linear actuator (13) to move the coil (1) along an x-axis following a seventh path (106) or a ninth path (108) or an eleventh path (110). That allows the coil (1) to move towards or away from the body (C).

Figure 10:
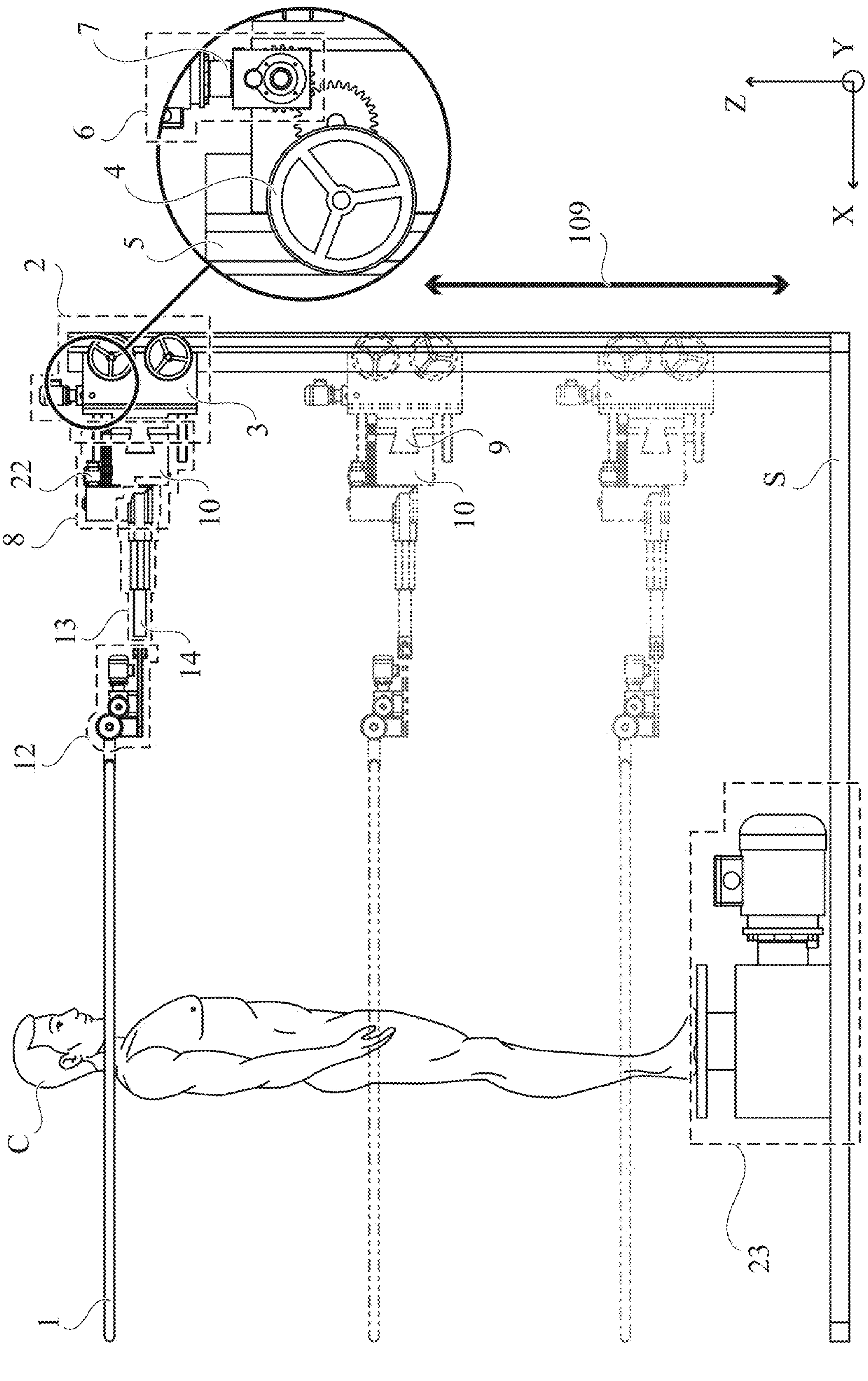
FIG. 10 shows an example a particular path of the directions of movement and twists in two degrees of freedom that the present disclosure and the mechanism of movements allow.
Figure 12:
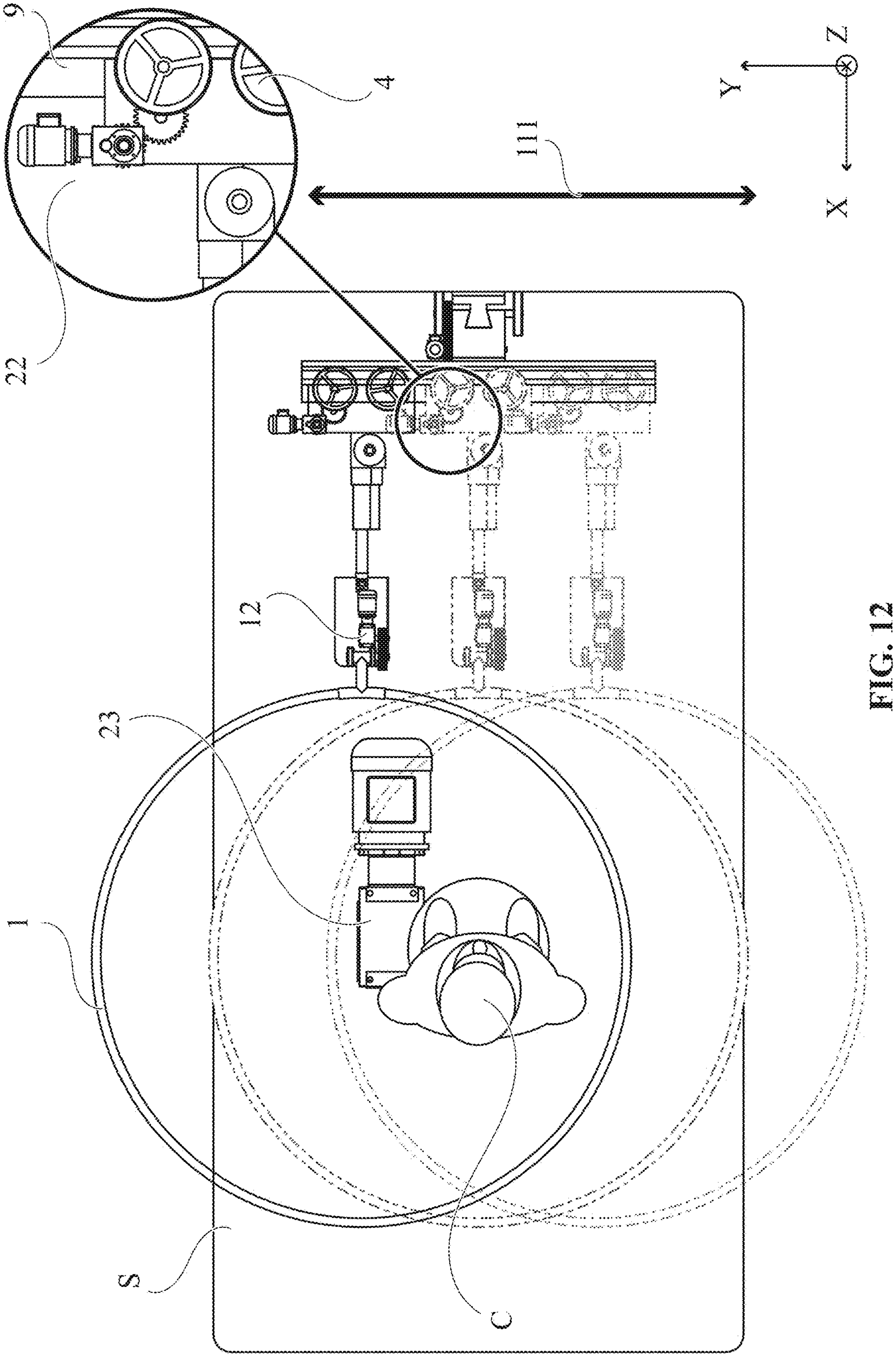
FIG. 12 shows a particular embodiment with the directions of travel and rotation in two degrees of freedom that incorporates a rotating base that allows the present disclosure.

Referring to FIG. 7, FIG. 10 and FIG. 12, in another example, the magnetic stimulation machine of the present disclosure comprises: a coil (1) that generates a magnetic field, an angle actuator (12) connected to the coil (1), and a first displacement mechanism (2) connected to a support surface (S) and coupled to the angle actuator (12); where the first displacement mechanism (2) moves the coil (1) along a z axis; the angular actuator (12) rotates the coil (1) to change the orientation of the coil (1) and thereby changes the direction of the magnetic field that stimulates a body (C).

Alternatively, the first displacement mechanism (2) moves the coil (1) along a z-axis following an eighth path (107) or a tenth path (109).

The angular actuator (12) rotates the coil (1) to change the direction of the magnetic field that stimulates the body (C) following a thirteenth trajectory (112).

Optionally, in a particular example of the disclosed machine, the first movement mechanism (2) is connected to the coil (1) by means of an angle actuator (12); where the angular actuator (12) rotates the coil (1) to change the direction of the magnetic field according to a thirteenth trajectory (112).

In a particular embodiment, the first movement mechanism (2) is connected to a control circuit that controls the movement of the movement mechanism (2).

Alternatively, the movement of the first displacement mechanism (2) is commanded by an operator. The operator moves the coil (1) following a particular movement pattern to magnetically stimulate a tissue of a body (C). According to the above, the machine of the present disclosure can move the coil (1) to change the direction of the magnetic field.

The above is convenient for magnetically stimulating the body (C) from different angles. In addition, it is convenient because it allows the coil (1) to rotate to move the magnetic field away from the body (C). In this way, the stimulation of the magnetic field on the body (C) can be abruptly removed, thereby generating a magnetic dipole rearrangement in the body tissue (C).

Referring to FIG. 8, the linear actuator (13) can be connected to the angle actuator (12) by means of a mechanical coupling, for example, by means of fastening elements such as screws, bolts, pins, rivets, pin-wedges, similar elements known to a person skilled in the art, and combinations thereof. Also, the linear actuator (13) can connect to the angle actuator (12) by means of clamps, jaws, splined shaft connections where a female shaft with a coupling cavity is connected to the angle actuator (12) or first linear actuator mechanism (13) and a male shaft is coupled to the socket of the female shaft located in the linear actuator (13) or the angle actuator (12).

Optionally, the machine of the present disclosure allows the linear actuator (13) to move the coil (1) along an x-axis following a ninth path (108) that allows the coil (1) to move towards or away from the body (C).

For example, in the case that the angular actuator (12) is made up of a gearmotor that has a first transmission element connected to a second transmission element connected, the transmission elements that connect the angular actuator (12) and the coil (1) can be selected from the group consisting of belts, chains, racks, sprockets, pulleys, cogged pulleys, spur or helical gears, friction wheels, and combinations thereof.

Preferably, the transmission elements that connect the coil (1) with the angular actuator (12) include shafts that rest on bearings located on a platform connected to the linear actuator (13). Bearings are selected of the group comprising pedestal bearings, with tensioning pedestal, split, flange, oval flange and combinations of the above.

In addition, the pillow blocks include selected bushings and bearings. The bearings are selected from ball bearings, needle bearings, roller bearings, multi-row ball, needle, or roller bearings, and combinations thereof.

Furthermore, in the case that the angular actuator (12) includes a motor or a gearmotor, preferably said motor or a gearmotor is connected on the platform of the linear actuator (13) with fixing elements selected from the group comprising screws, bolts, rivets, pin-wedges, rivets, similar elements known to a person skilled in the art, and combinations thereof.

Figure 9:
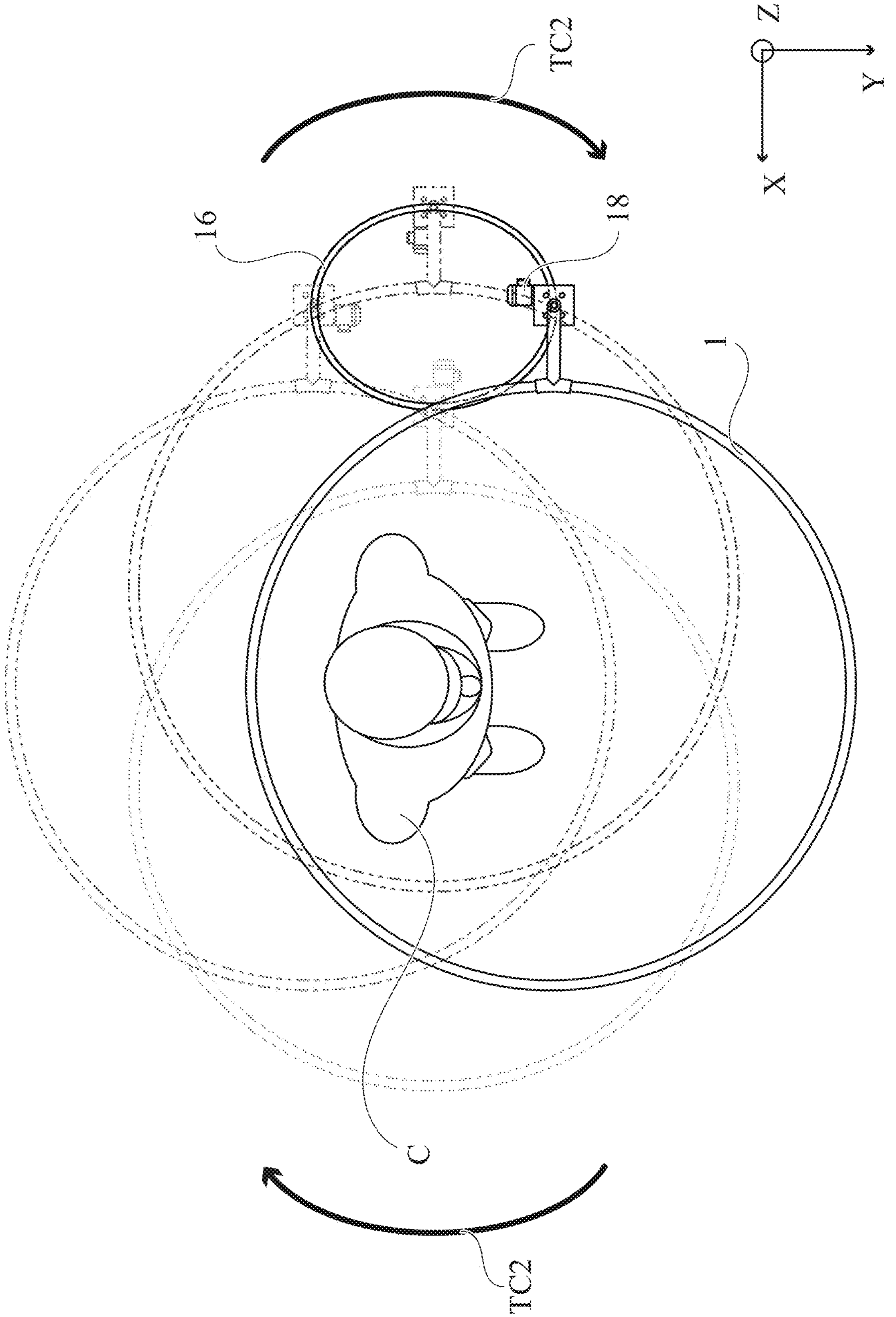
FIG. 9 shows an example a particular path of the directions of travel and twists in two degrees of freedom that the present disclosure allows along the body of a subject in a top and superimposed view.

Referring to FIG. 7, FIG. 8 and FIG. 9, optionally, the machine of the present disclosure may have a fourth displacement mechanism (15) connected between the linear actuator (13) and the second displacement mechanism (8); the fourth displacement mechanism (15) is made up of:

a second curved guide connected to the second displacement mechanism (8);

a fourth carriage movably connected to the second curved guide; and a fourth drive mechanism connected to the fourth carriage;

where the fourth driving mechanism moves the fourth carriage along the second curved guide, and the fourth displacement mechanism (15) moves the coil (1) in a second predetermined path (TC2).

Optionally, the fourth displacement mechanism (15) moves the coil (1) in a third predetermined path (TC3) in the opposite direction to the direction of the second predetermined path (TC2).

In this case, the machine of the present disclosure can move the magnetic field generated by the coil (1) in a second predetermined path (TC2), whereby a curved path can be generated with the magnetic field on the body (C).

For example, when the angle actuator (12) arranges the coil (1) so that the magnetic field is projected vertically, the third displacement mechanism (11) can move the magnetic field in a second predetermined path (TC2). Preferably, the second predetermined path (TC2) is closed and the magnetic field moves cyclically.

Furthermore, by means of the first displacement mechanism (2) the magnetic field generated by the coil (1) can be displaced in the z axis, while the fourth displacement mechanism (15) moves the magnetic field in the second predetermined path (TC2). In this way, a stimulation with a helical path of the magnetic field can be generated striking the body (C).

The geometry of the second predetermined path (TC2) is defined by the geometry of the second curved guide. The second curved guide can be circular, elliptical, polygonal in shape with rounded corners (eg square, rectangular, triangular, pentagonal, hexagonal, octagonal, or polygonal with more than three sides). Also the geometry of the first curved guide (16) can be formed from curves with variable radius of curvature. Preferably, the first curved guide (16) is closed, whereby the third carriage can move cyclically and continuously.

Likewise, the second curved guide can be formed from rails with a T, or L cross section. Also, the second curved guide can be formed from profiles with an I, U, C or T cross section.

For its part, the fourth carriage can be similar to the first carriage (3) and the second carriage (10). Also, the fourth driving mechanism may be similar to the first driving mechanism (6).

Preferably, the fourth carriage has rolling elements (4) that travel on the second curved guide, where one of the rolling elements (4) is driven by the fourth driving mechanism. Furthermore, the fourth driving mechanism is preferably an electric gearmotor.

On the other hand, the first guide (5), second guide (9), first curved guide (16), and second curved guide are preferably selected from the group comprising metals such as carbon steel, cast iron, galvanized iron, chromium steels, chromium-nickel steels, chromium-nickel-titanium steels, nickel-chromium-molybdenum-tungsten alloy, ferrous chromium-moly alloys, 301 stainless steel, 302 stainless steel, 304 stainless steel, stainless steel 316, 405 stainless steel, 410 stainless steel, 430 stainless steel, 442 stainless steel, manganese alloy steel, aluminum, brass, plastic materials such as polyvinyl chloride (PVC); chlorinated polyvinyl chloride (CPVC); polyethylene terephthalate (PET), polyamides (PA) (e.g. PA12, PA6, PA66); polychlorotrifluoroethylene (PCTFE); polyvinylidene fluoride (PVDF); polytetrafluoride ethylene (PTFE); ethylene-chlorotrifluoroethylene (ECTFE); fiber-reinforced plastics (polyester, vinyl ester, epoxy, vinyl resins) (eg glass, aramid, polyester), woods (eg conifers such as pine, oak and walnut, broadleaf, fir, larch, spruce, other woods suitable for structural use known to a person skilled in the art), polymers (eg polyester, vinylester, epoxy, vinyl resins), reinforced with fibers (eg polyester, glass, aramid, carbon), other materials for structural use known to a person skilled in the art matter, and combinations thereof, for its acronym in English); polyvinylidene fluoride (PVDF); polytetrafluoride ethylene (PTFE); ethylene-chlorotrifluoroethylene (ECTFE); fiber-reinforced plastics (polyester, vinyl ester, epoxy, vinyl resins) (eg glass, aramid, polyester), woods (eg conifers such as pine, oak and walnut, broadleaf, fir, larch, spruce, other woods suitable for structural use known to a person skilled in the art), polymers (eg polyester, vinylester, epoxy, vinyl resins), reinforced with fibers (eg polyester, glass, aramid, carbon), other materials for structural use known to a person skilled in the art matter, and combinations thereof.

Referring to FIG. 10, in one example, the first displacement mechanism (2) may be a carriage-guide mechanism that includes a first carriage (3), which moves along a first guide (5). For example, the first carriage (3) may have rolling elements (4) that engage the first guide (5). The rolling elements (4) are selected from the group consisting of wheels, rubber wheels, wheel wheels covered with rims, wheels for rails, roller casters, similar elements known to a person skilled in the art or and combinations thereof.

For its part, the first guide (5) can be a rail or a structural profile. The first guide (5) can be selected from the group comprising T-rails, L-rails. Also, the first guide (5) can be selected from structural profiles with I, U, C, or T cross-section, the first guide (5) and the first carriage (3) can be connected by a dovetail joint.

Referring to FIG. 10 and FIG. 12, for example, the z-axis can extend vertically, whereby the movement of the first displacement mechanism (2) along the first guide (5) allows the height of the coil (1) to be changed. In this case the first guide (5) is connected to a support surface (S) that is arranged horizontally.

Preferably, said a support surface (S) is selected from a level floor, a concrete mortar, a platform, a platform with levelers arranged on a floor, a pallet floor, or a table, similar support surfaces known to a person versed in the matter, and combinations thereof.

For example, if the support surface (S) is a level floor or a platform with levelers, it is ensured that the first guide (5) is in a vertical position, with which the coil (1) can move along the axis z without deviations.

Referring to FIG. 10, the first carriage (3) can be connected to a first driving mechanism (6) that generates the movement of the first carriage (3) along the first guide (5). Furthermore, the first guide (5) can include a rack that is connected to a gear arranged in a rolling element (4) of the first carriage (3). The gear connects to the first driving mechanism (6) with transmission elements selected from gears, toothed belts, chains, chain sprockets and combinations thereof.

Optionally, the first motive mechanism (6) is selected from electric motors, internal combustion motors, pneumatic motors, hydraulic motors, or gear motors, other types of equivalent motors known to a person skilled in the art, and combinations thereof.

The first driving mechanism (6) is connected on the first carriage (3) so that it travels on it.

On the other hand, optionally the first driving mechanism (6) can be arranged in a raised position greater than a maximum working height of the machine. In this case, the first motive mechanism (6) can be connected to the first carriage (3) by means of cables, chains, belts, and combinations thereof, so that the first carriage (3) hangs from the first motive mechanism (6). This option makes it possible to avoid loading the first driving mechanism (6) on the first carriage (3), thereby saving energy during the operation of the first moving mechanism (2).

On the other hand, in the case that the first motor mechanism (6) is selected between electric motors, these can be selected between stepper motors, squirrel cage motors, asynchronous motors, direct current motors, motors with assisted start and combinations of these.

Also, in the case of gearmotors, these can be selected from the group comprising worm gearmotors, gearmotors, cycloidal gearboxes, planetary gearmotors, internal gear reducers, external gear reducers, other gearmotors known to a person skilled in the art, matter, and combinations of the above.

It will be understood in the present disclosure that a gearmotor includes a motor and a reduction gear that varies the torque and speed of said motor. Geared motor can be selected from electric motors, internal combustion engines, air motors, hydraulic motors. Preferably, the gearmotors have electric motors.

Furthermore, the first carriage (3) can also be driven with a first manual force motive mechanism (6), for example, with levers, pulleys, or hoists that are connected to the first carriage (3).

Optionally, first driving mechanism (6) is selected from mechanical winches, electric winches, chain, belt, cable traction mechanisms, adhesion winches, drum winches, similar winches known to a person skilled in the art and combinations thereof.

For example, the first carriage (3) is connected to the first motive mechanism (6) by traction elements selected from cables, belts, chains, and combinations thereof. In this way, the first guide (5) makes it possible to keep the first carriage (3) aligned on the z-axis while the first driving mechanism (6) exerts the force to move the first carriage (3).

Optionally, the first driving mechanism (6) is connected to a braking device (7). In this case, the braking device (7) is selected from the group comprising electro-brake brakes (eg electromagnet, electro-hydraulic brakes, motor-built brakes), counter-current braking, DC injection braking, other braking devices known to a person skilled in the art, and combinations thereof.

For example, electromagnet brakes or electro-hydraulic brakes consist of a disc connected to a power shaft of the first drive mechanism (6) and shoes that hug the disc when the brake is activated.

In particular, the electromagnet brake has an electrical circuit that detects when the First drive mechanism (6) is activated and keeps the brake shoes open. When the electrical circuit does not detect that the first motor mechanism (6) is activated, it closes the shoes, blocking the power shaft of the first motor mechanism (6).

For its part, the electrohydraulic brake comprises a hydraulic system with a hydraulic pump, an actuator connected to the shoes, and a solenoid valve connected between the actuator and the hydraulic pump. The solenoid valve has an electrical circuit that detects when the First drive mechanism (6) is activated and keeps the brake shoes open. When the electrical circuit does not detect that the first motor mechanism (6) is activated, it closes the shoes, blocking the power shaft of the first motor mechanism (6).

On the other hand, in the case that the first movement mechanism (2) has a first motor mechanism (6) of manual operation, the first carriage (3) can include a braking device (7) of manual operation, for example, a braking device (7) with wedge mechanisms, presses, pins or jaws that block the first carriage (3) against the first guide (5).

Also, in the example case in which the first driving mechanism (6) is manually operated that operates with cables, the first driving mechanism (6) may include a pulling cable and a safety cable. The cables are coupled to an emergency brake that has acceleration sensors that allow detecting if the tractor cable has broken, thereby activating the emergency brake by blocking the safety cable.

Locking the safety cable is important to prevent the coil (1) from falling out of control. If the coil (1) were to fall uncontrollably, it could hit the body (C). In addition, in the case that the body (C) is a living being, the coil (1) can hit it causing damage to the living being.

On the other hand, the first displacement mechanism (2) can be connected to the angle actuator (12) by means of a mechanical coupling, for example, by means of fixing elements selected between screws, bolts, pins, rivets, pin-wedges, similar elements known to a person skilled in the art, and combinations thereof.

Also, the first displacement mechanism (2) can be connected to the angle actuator (12) by means of clamps, jaws, splined shaft connections where a female shaft with a coupling cavity is connected to the angle actuator (12) or first displacement mechanism (2) and a male shaft is coupled to the socket of the female shaft located in the first displacement mechanism (2) or the angle actuator (12).

Preferably, the angle actuator (12) is mechanical and includes a motor or gearmotor connected to a pinion-chain, or pinion-rack or worm gear mechanism. In this case, the angular actuator (12) can include a braking device (7) as the braking device (7) of the first displacement mechanism (2).

The braking device (7) can be coupled to the motor or gearmotor of the angle actuator (12). The braking device (7) makes it possible to brake the motor and keep the angular actuator (12) in a fixed angular position, whereby the coil (1) can be tilted and kept in a desired angular position.

Likewise, the motor or gearmotor of the angle actuator (12) can be similar to the first motor mechanism (6).

On the other hand, the angular actuator (12) is selected from pneumatic, hydraulic, mechanical, electromechanical actuators and combinations thereof. Such pneumatic, hydraulic, mechanical, electromechanical actuators may include single-acting, double-acting, spring-assisted return, pneumatic or valve-assisted hydraulic actuators (eg distribution, blocking, regulators, sequential, solenoid valves), mechanical actuators, with motors, geared motors, and power transmission mechanisms (eg toothed pulleys, pinions, chain sprockets, spur gears, helical gears, chains, toothed belts, and combinations thereof), and combinations thereof.

For example, the angular actuator (12) is made up of a gearmotor that has a first transmission element connected to a second transmission element connected, where the second transmission element is connected by means of a shaft to the coil (1). The axis that is connected to the coil (1) allows the angle of the coil (1) to be changed by rotating it with respect to an x, and or z axis. Preferably, the coil rotates about an x or y axis.

In this case, the transmission elements that connect the angle actuator (12) and the coil (1) can be selected from the group comprising belts, chains, racks, chain sprockets (sprocket, in English), pulleys, toothed pulleys, gears straight or helical, friction wheels and combinations thereof.

Preferably, the transmission elements that connect the coil (1) with the angular actuator (12) are arranged on bearings located on a platform connected to the first displacement mechanism (2). Bearings are selected of the group that includes bearings with tensioning pedestal, split, flange, oval flange and combinations of the above.

On the other hand, in another embodiment of the magnetic tissue stimulation machine of the present disclosure, it comprises:

a coil (1) that generates a magnetic field;

an angle actuator (12) connected to the coil (1);

a first displacement mechanism (2) connected to a bearing surface (S) and coupled to the angle actuator (12); and a linear actuator (13) connected between the angle actuator (12) and the first displacement mechanism (2);

where the linear actuator (13) allows the coil (1) to be moved along an x axis, the first movement mechanism (2) moves the coil (1) along a z axis, the angle actuator (12) turn the coil (1) to change the direction of the magnetic field, and the magnetic field stimulates a body (C).

In this case, the machine of the present disclosure allows the linear actuator (13) to move the coil (1) along an x axis. Preferably, the x-axis is orthogonal to the z-axis. The displacement in the x-axis of the coil (1) makes it possible to generate a linear movement of the magnetic field, with which a path in the x-axis of said magnetic field can be generated on the body (C).

Furthermore, the linear actuator (13) can be activated simultaneously with the first displacement mechanism (2), in order to generate an axial travel with the magnetic field on the body (C).

Optionally, the machine of the present disclosure allows the linear actuator (13) to move the coil (1) along an x-axis following a seventh path (106). That allows the coil (1) to move towards or away from the body (C).

Figure 13:
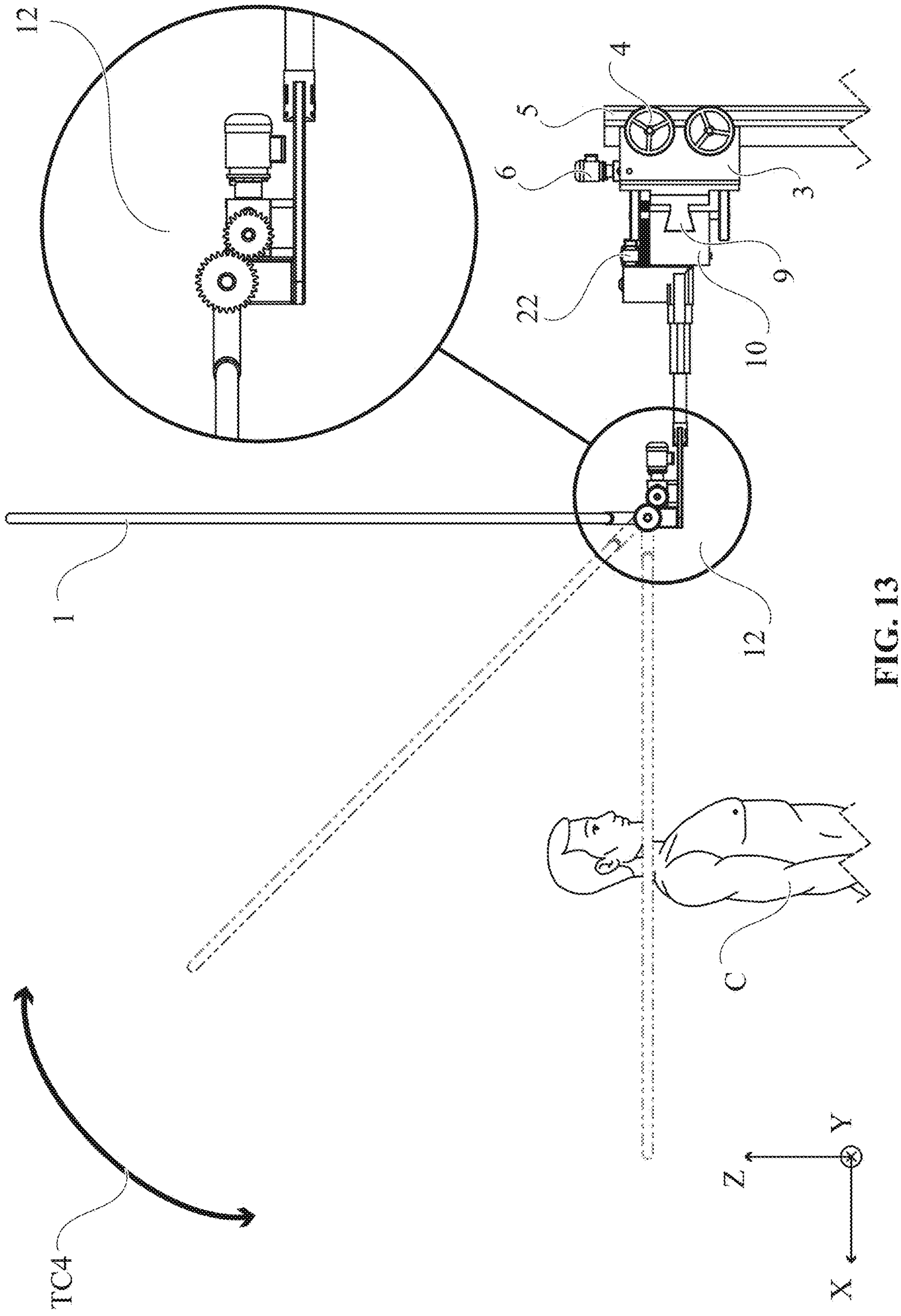
FIG. 13 shows a particular embodiment in which an angle actuator changes the direction of the magnetic field applied to the body.

Additionally, the angle actuator (12) can arrange the coil (1) so that the magnetic field is oriented horizontally. For example, in FIG. 7 and FIG. 13 shows a coil (1) of circular shape that is arranged vertically by means of the angular actuator (12), whereby the magnetic field is projected axially from the coil (1) along the x-axis.

Alternatively, in a particular embodiment of the machine of the present disclosure, the angular actuator (12) rotates the coil (1) in a fourth predetermined path (TC4), changing the angle between the axis of the coil (1) and the longitudinal axis, of the tissue.

In this way, the magnetic field impinges on the body (C) in a direction orthogonal to the longitudinal axis of said body (C). For example, in the case that the body (C) is a human body, the magnetic field can impinge on the anterior part of the human body. Also, if the human body is turned, the magnetic field can impinge on the back or side of the body (C).

In the same way, the machine can actuate the first displacement mechanism (2) to move the coil (1) along the z-axis. Returning to the example in which the body (C) is a human body, the first movement mechanism (2) can move the coil (1) along the body (C), thereby generating a path with the magnetic field in the direction of the z axis.

On the other hand, the linear actuator (13) is selected from the group comprising pneumatic, hydraulic, mechanical, electromechanical actuators and combinations thereof. Optionally, pneumatic, hydraulic, mechanical, electromechanical actuators are selected from single-acting, double-acting, spring-assisted return, pneumatic, or valve-assisted hydraulic actuators (eg distribution, blocking, regulators, sequential, solenoid valves), and combinations thereof.

Referring to FIG. 10, an embodiment of the magnetic tissue stimulation machine of the present disclosure is taught comprising:

a coil (1) that generates a magnetic field;

an angle actuator (12) connected to the coil (1);

a first displacement mechanism (2) connected to a bearing surface (S) and coupled to the angle actuator (12);

a second displacement mechanism (8) connected between the first displacement mechanism (2) and the angle actuator (12); and a linear actuator (13) connected between the angle actuator (12) and the first displacement mechanism (2);

where the linear actuator (13) allows the coil (1) to be moved along an x axis, the first movement mechanism (2) moves the coil (1) along a z axis, the angle actuator (12) The coil (1) rotates to change the direction of the magnetic field, the second displacement mechanism (8) moves the coil (1) along a y-axis, and the magnetic field stimulates a body (C).

According to the above, the coil (1) can move along the axis y which is preferably orthogonal to a longitudinal axis of the stimulated body (C). This movement in the transverse direction can be generated by mechanically connecting the coil (1) to a second displacement mechanism (8). In this case the second displacement mechanism (8) is connected between the first displacement mechanism (2) and the angle actuator (12); where the second displacement mechanism (8) moves the coil (1) along a y-axis.

Likewise, the combination of the first displacement mechanism (2), angular actuator (12), linear actuator (13), and the second displacement mechanism (8) allows the coil (1) to be moved three-dimensionally with respect to a system of coordinate axes and orthogonal x, y, z, and allows the coil (1) to rotate with respect to one of the axes of the coordinate system by means of the angular actuator (12). Accordingly, the magnetic field can be oriented to travel the body (C) along straight, curved, helical paths, and combinations thereof.

Optionally, the first displacement mechanism (2), angle actuator (12), linear actuator (13), and the second displacement mechanism (8) are electrically actuated by means of a computing unit.

The computing unit allows to define an actuation sequence by means of a movement pattern of the first displacement mechanism (2), angle actuator (12), linear actuator (13), and the second displacement mechanism (8) to trace a predetermined path (eg straight, curved, inclined) for the displacement of the coil (1) that generates a magnetic field.

For its part, the second displacement mechanism (8) is selected among others from the group that includes winches, cranes, pneumatic, hydraulic, mechanical or electromechanical actuation cylinders, single-acting cylinders, double-acting cylinders, gantries fitted with hoists of chain, cable, or strap, where the hoists can include skids that allow a movement orthogonal to the longitudinal direction, scissor lifts, trolley-guide mechanisms; and combinations thereof.

Also, the second displacement mechanism (8) can be a mechanism operated with manual force, for example, by levers, pulleys, hoists.

Referring to FIGS. 10, FIG. 11 and FIG. 12, for example, the second displacement mechanism (8) can be a carriage-guide mechanism like the first displacement mechanism (2). In this case, the second displacement mechanism (8) is a carriage-guide mechanism that includes a second guide (9) connected to the support surface (S); and a second carriage (10) movably coupled to the second guide (9). Likewise, the second movement mechanism (8) has a second motor mechanism (22) connected to the second carriage (10) where the second motor mechanism (22) moves the second carriage (10) along the second guide (9) of according to a thirteenth trajectory (112).

The second driving mechanism (22) can be of the same type as the first driving mechanism (6), and can include a braking device (7) that allows to fix the position of the coil (1) in a position of the y-axis.

Likewise, the second movement mechanism (8) can include a rack arranged in the second guide (9) that is connected to a gear arranged in a rolling element (4) of the second carriage (10).

Referring to FIG. 10 and FIG. 12, optionally, the machine also includes a rotating platform (23) located on the support surface (S), where the body (C) is arranged on the rotating platform (23). The rotating platform (23) allows the body (C) to be rotated to change the area of incidence of the magnetic field produced by the coil (1).

The turntable (23) includes a driving mechanism selected from motors, geared motors, levers, crank mechanisms, gear mechanisms, chain mechanisms, pinion mechanisms, chain sprocket mechanisms, pulley mechanism, toothed pulley mechanisms, and combinations thereof.

Preferably, the turntable (23) rests on a structure that has movable supports that allow the rotary movement of said turntable (23). For example, movable bearings can be ball joints, bearings, bearings, concentric discs, and combinations thereof.

For example, the turntable (23) includes a table anchored to the support surface (S). The table has a horizontal platen that includes a bearing that engages a moving shaft. The moving shaft is connected to a rotary table on which the body (C) is arranged. In addition, the moving shaft is connected to the driving mechanism, which is a gearmotor, through a transmission of helical pinions connected at 90 degrees.

Referring to FIG. 8, FIG. 9 and FIG. 10, on the other hand, the machine of the present disclosure in a particular example includes a third displacement mechanism (11) connected between the angular actuator (12) and the linear actuator (13), the third displacement mechanism (11) is connects to a distal end of a stem (14) of the linear actuator (13); the third displacement mechanism (11) is made up of:

a first curved guide (16) connected to the stem (14);

a third carriage movably connected to the first curved guide (16); and a third drive mechanism (18) connected to the third carriage.

where the third driving mechanism (18) moves the third carriage along the first curved guide (16), and the third displacement mechanism (11) moves the coil (1) in a first predetermined path (TC1).

In addition, by means of the linear actuator (13) the magnetic field generated by the coil (1) can be displaced in the x-axis, while the third displacement mechanism (11) moves the magnetic field in the first predetermined path (TC1). In this way, a magnetic stimulation with a helical path can be generated along the tissue of a body (C).

The geometry of the first predetermined path (TC1) is defined by the geometry of the first curved guide (16). The first curved guide (16) can be circular, elliptical, polygonal in shape with rounded corners (eg square, rectangular, triangular, pentagonal, hexagonal, octagonal, or polygonal with more than three sides). Also the geometry of the first curved guide (16) can be formed from curves with variable radius of curvature. Preferably, the first curved guide (16) is closed, whereby the third carriage can move cyclically and continuously.

Likewise, the first curved guide (16) can be formed from rails with a T, or L cross section. Also, the first curved guide (16) can be formed from profiles with an I, U, or L cross section. C, or in T.

Referring to FIG. 8, FIG. 9 and FIG. 10, for its part, the third carriage may be similar to the first carriage (3) and the second carriage (10). Also, the third drive mechanism (18) may be similar to the first drive mechanism (6).

Preferably, the third carriage has rolling elements (4) that travel on the first curved guide (16), where one of the rolling elements (4) is driven by the third driving mechanism (18). Furthermore, the third driving mechanism (18) is preferably an electric gearmotor.

Figure 14:
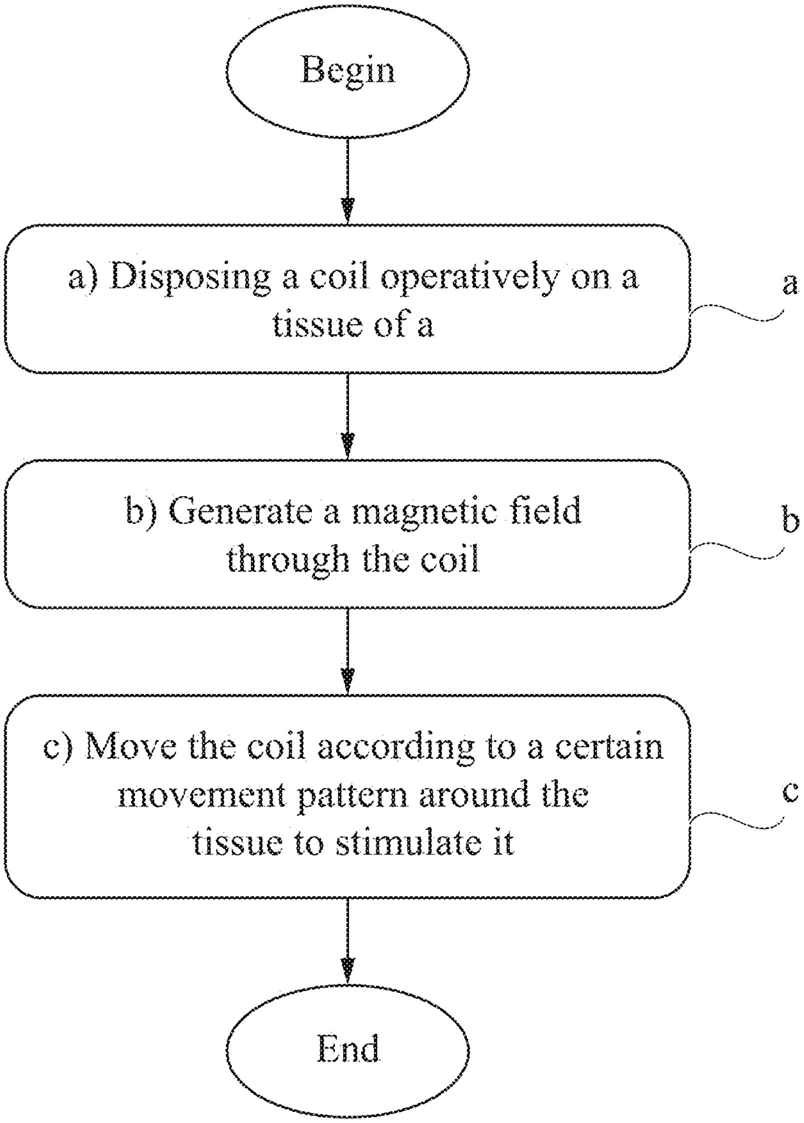
FIG. 14 shows a flow chart of a particular embodiment of a method for magnetic stimulation of tissues of the present disclosure.

On the other hand, referring to FIG. 14, a flow chart of a particular embodiment of the method of magnetic stimulation of tissues of a body (C) of the present disclosure is shown which comprises the following steps: a) disposing a coil (1) operatively on a tissue of a body (C); b) generating a magnetic field by means of the coil (1); and c) moving the coil (1) according to a determined movement pattern around the tissue to stimulate it.

In an embodiment of the method disclosed herein, in step a) arranging a coil (1) operatively on a tissue of a body (C), corresponds to locating the coil (1) in a position in three-dimensional space at a determined distance from body tissue (C).

In a particular embodiment of the method disclosed in this document, the distance between the coil (1) and the tissue varies according to a movement pattern that is established by an operator, being defined in a computing unit that implements said method, or simply have an operator follow the steps of the method described throughout this document.

In a particular example, referring to FIG. 2, a body (C) that corresponds to a human is shown, the arrangement of the coil (1) corresponds to a point in three-dimensional space around said body (C), in which the axis of the coil (1) is coaxial to the longitudinal axis of the body (C), and the coil (1) is at the height of the soles of the feet of said body (C).

Also, said arrangement of the coil (1) is not limited to the sole of the feet and in other embodiments of the disclosed method, it corresponds to a point in three-dimensional space where the body (C) may or may not be.

In the same example of the method disclosed and described hereinabove, the action of disposing the coil (1) is performed by a machine for magnetic tissue stimulation controlled by a computing unit, such as the machine of the present disclosure.

In other examples of the method herein, the action of arranging the coil (1) is performed by an operator holding the coil (1).

In an embodiment of the method of the present disclosure in step b), the magnetic field generated by the coil (1) obeys an activation signal.

In said embodiment, the activation signal received by the coil (1) is a signal that is selected from an alternating current signal, or direct current, pulsed, alternating or non-alternating pulse train, square wave, triangle wave, tooth wave of saw, amplitude modulated wave, frequency modulated wave, phase modulated wave, pulse position modulated wave, cycle variation wave or combinations of these. This signal is generated by a computing unit or by a signal generator or combinations of the above based on programs and feedback.

In this particular embodiment of the method of the present disclosure, the programs referred to in the present document correspond to information encoded or not encoded in a computing unit, said programs modify all the parameters of the activation signal that activates the coil (1). For example, the program can be a file in binary encoding that is embedded in a microcontroller (computer unit of the control circuit) that executes a logical sequence of steps.

Optionally, in another embodiment of the method of this disclosure, the computing unit allows one or more trigger signals to be applied to an array of coils, in a sequentially determined time, out of phase with another trigger signal or multiple signals, of stimulation, randomly or obeying a program established for each of the coils (1) of the coil array.

In particular examples of the method of the present disclosure, the drive signal is a signal from an alternating current source with a voltage between about 330 Vac to about 20 kVac at frequencies between about 0.1 Hz and about 50 KHz, for example, 120 Vac at 60 Hz, 120 Vac at 50 Hz, 220 Vac at 60 Hz, 220 Vac at 50 Hz. However, the coil (1) can operate in direct current.

In another example of the disclosed method, in step c) the movement pattern follows a path about a longitudinal axis of the tissue.

Optionally, the movement pattern adjusts to the degrees of freedom of the magnetic tissue stimulation machine disclosed in this document.

In this document, when talking about the degrees of freedom of the stimulation machine, it refers to the movement of the parts that the machine comprises in a three-dimensional space, such as the translation in the three perpendicular axes that, for example, allows vertical movements, horizontal, forward, backward, left, right, up and down, rotation or combination of previous movements.

In another example of the method of the present disclosure, in step b) the generated magnetic field has an intensity between approximately 0.1 mT and approximately 200 mT. In these ranges of magnetic field intensity it is possible to optimally stimulate the tissue without damaging it.

In another example of the method of the present disclosure, in step b) the generated magnetic field has an intensity between approximately 40 mT and approximately 200 mT. In these ranges of magnetic field intensity it is possible to optimally stimulate the tissue without damaging it.

Optionally, it is possible that in step a) and in step c) an operator performs the actions of locating and moving the coil.

Alternatively, in step a) and in step c) a movement mechanism executes the actions of locating and moving the coil.

In a different embodiment of the method of the present disclosure, in step b) the activation signal is generated by an electrical and magnetic stimulation device.

Optionally, in a particular example of the device and method of the present disclosure, in step c), the activation signal is generated by an electrical and magnetic stimulation device such as the one disclosed in patent application NC2017/0011756, entitled "Device for electrical and magnetic stimulation of tissues." This device provides the electrical current to the coil (1) of the magnetic stimulation machine described herein and provides the variation of the magnetic field.

In this same example, another computing unit can control the movement of the machine of the present disclosure.

In a particular example of the method of the disclosure, in step c), the movement pattern includes trajectories in three dimensions that are selected from the group of rectilinear trajectories, curvilinear trajectory (circular, parabolic, elliptical, helical, conical helix, spiral), and combinations of these.

In another example of the method of the disclosure, in step c), the movement pattern changes the orientation of the coil. The orientation of the coil changes relative to the tissue, in particular it changes relative to a longitudinal axis of the tissue.

Figure 15:
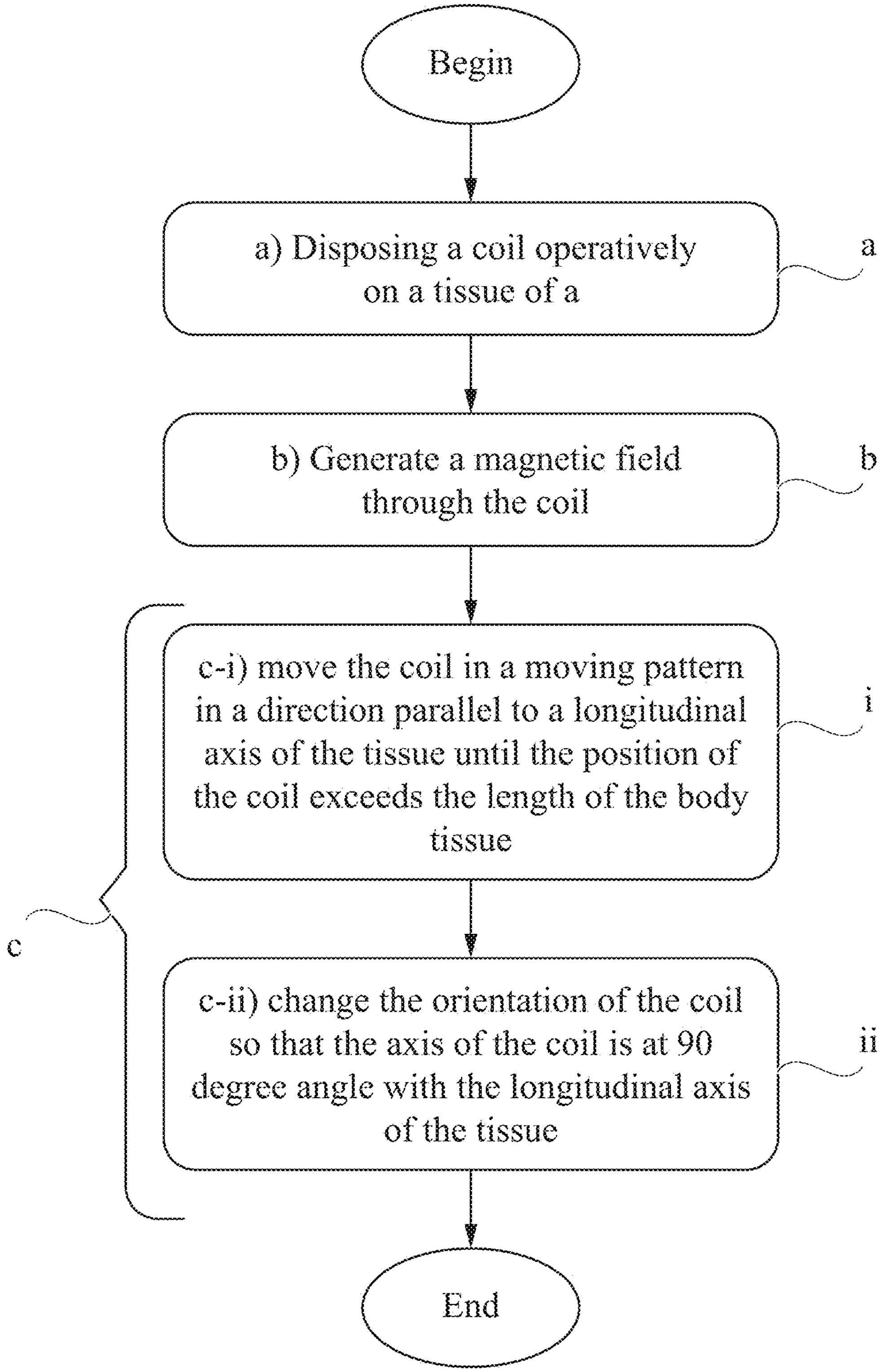
FIG. 15 shows a flow chart of a particular embodiment of a method for the magnetic stimulation of tissues with sub-steps i and ii for step c, of the present disclosure.

Referring to FIG. 15, a flow chart of a particular embodiment of another embodiment of the method of the disclosure is shown, in which, in step c) the movement pattern performs the following sub-steps:

i) moving the coil (1) following a movement pattern in a direction parallel to a longitudinal axis of the tissue until the position of the coil (1) exceeds the length of the body tissue (C); and ii) changing the orientation of the coil (1) so that the axis of the coil (1) forms an angle of 90 degrees with the longitudinal axis of the tissue.

The above embodiment makes it possible to abruptly remove the stimulation of the magnetic field on the body (C), thereby generating a magnetic dipole reorganization in the body tissue (C).

For the understanding of this document, the movement pattern refers to a series of actions or movements organized in a sequence, the combination of which allows the movement of the coil (1) and consequently the movement of the magnetic field vector in a three-dimensional space, around the body (C) containing a tissue to be stimulated.

In a particular example of the method of the present disclosure, sub-step ii) corresponds to removing the electrical supply from the coil. This allows to disruptively remove the field stimulation that stimulates the tissue, allowing the configuration of the polarization of each of the tissue particles to remain invariant at the end of the stimulation of said tissue.

Figure 16:
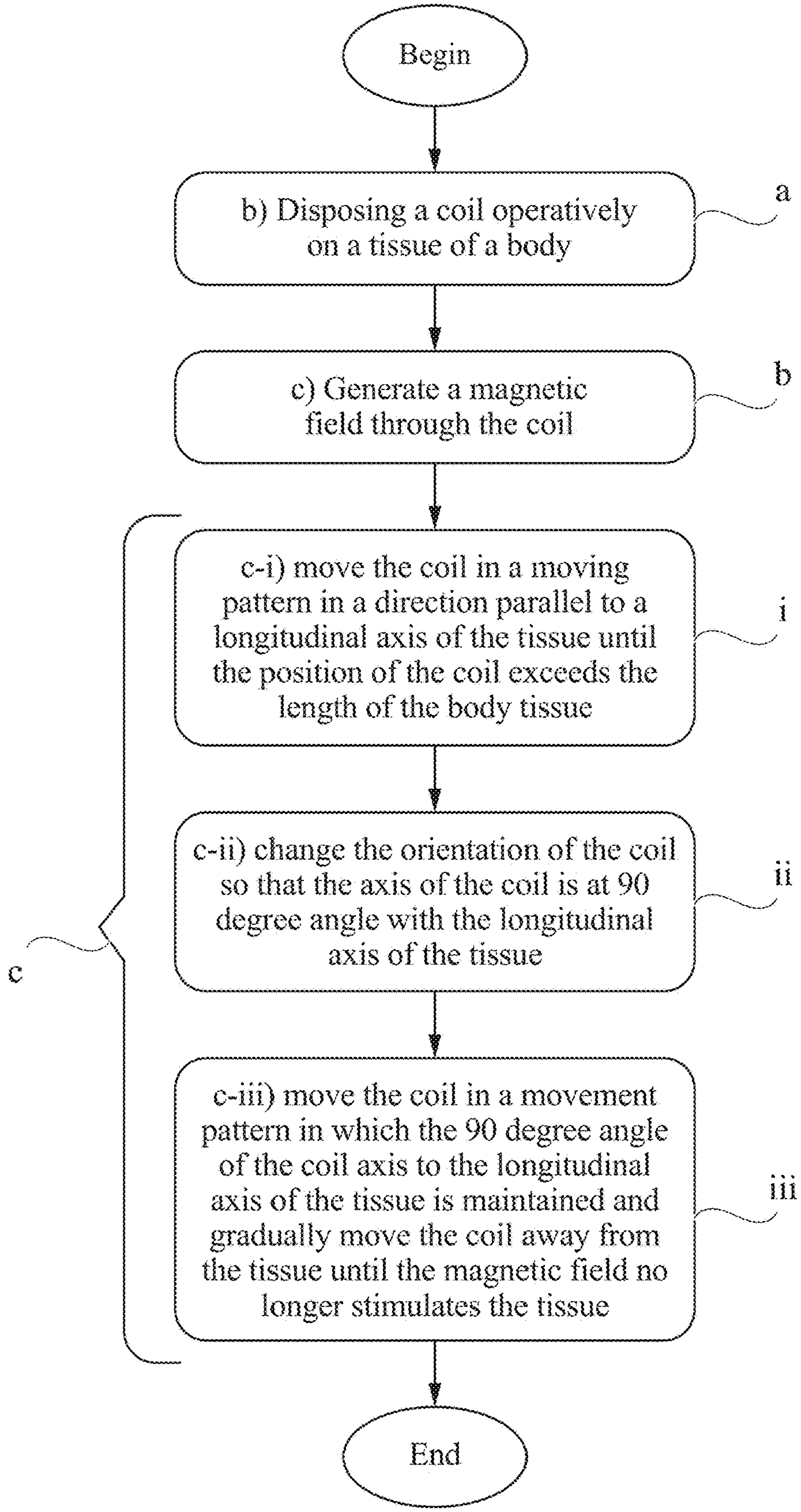
FIG. 16 shows a flow chart of a particular embodiment of a method for the magnetic stimulation of tissues with sub-steps i, ii and iii for step c, of the present disclosure.

Referring to FIG. 16, a flow chart of another particular embodiment of the disclosed method is shown, in which, after sub-step ii) a sub-step iii) follows, in which a second pattern of moving the coil is followed while maintaining the angle 90 degrees to the longitudinal axis of the tissue and gradually move the coil of tissue away from the tissue. This allows the tissue to gradually stop stimulating and leave a magnetic dipole reorganization of the body's tissue cells (C) established.

Example 1: Magnetic Stimulation Machine with Four Degrees of Freedom

In one embodiment of the disclosure the machine has a coil (1) that is a Helmholtz coil that operates with a voltage between 330 V and 20 kV, and generates a magnetic field in the body between 0.1 mT and 200 mT, and preferably between 40 mT and 200 mT.

In this case the body (C) is a human being as illustrated in FIG. 10, in addition, the machine has a mechanical angle actuator (12) and includes a gearmotor with a braking device (7) of the electromagnet type. The gearmotor is bolted to a platform located on a linear actuator (13). Furthermore, the gearmotor of the angular actuator (12) has a first transmission element connected to a second transmission element, where the transmission elements that connect the coil (1) with the angular actuator (12) include shafts that support each other on single row ball bearing pillow blocks. The bearings are bolted to the deck.

On the other hand, the machine has a first movement mechanism (2) and a second movement mechanism (8), where both movement mechanisms (2, 8) are carriage-guide mechanisms. Each carriage-guide mechanism includes a carriage (3, 10), which has rolling elements (4) that engage the first guide (5, 9).

Each guide (5,9) is a T-profile on which the rolling elements (4) rest. In addition, each guide (5,9) has a rack that connects to a gear arranged in a rolling element (4) of the carriage (3, 10), where both movement mechanisms (2, 8) have driving mechanisms (6, 22), which are geared motors connected to the gear of the rolling element (4) where each movement mechanism (2, 8) is connected to the carriage (3, 10) with means of bolts.

On the other hand, the first movement mechanism (2), angle actuator (12), linear actuator (13), and the second movement mechanism (8) are connected to a programmable logic controller (PLC).

In this embodiment of the disclosure, the combination of the first displacement mechanism (2), angle actuator (12), linear actuator (13), and the second displacement mechanism (8) allows the coil (1) to be moved three-dimensionally with respect to a system of coordinate and orthogonal axes x, y, z, and allows the coil (1) to rotate with respect to one of the axes of the coordinate system by means of the angular actuator (12).

Accordingly, the magnetic field can be oriented to travel the body (C) along straight, curved, helical paths, and combinations thereof.

The computing unit allows to define an actuation sequence by means of a movement pattern of the first displacement mechanism (2), angle actuator (12), linear actuator (13), and the second displacement mechanism (8) to trace a predetermined path (eg straight, curved, inclined) for the coil (1) generating the magnetic field. In turn, the magnetic field is generated by means of an activation signal with a square wave with a fixed useful cycle of 15%, a voltage of 330 volts peak to peak and a frequency of 1 kHz, the activation signal is programmed in the same computing unit.

Example 2: Magnetic Stimulation Machine with Five Degrees of Freedom

In another embodiment of the disclosure, the machine of example 1 was taken and a rotating platform (23) located on the support surface (S) was added, where the body (C) is arranged on the rotating platform (23). The rotating platform (23) includes a table anchored to the support surface (S). The table has a horizontal platen that includes a bearing that engages a moving shaft. The moving shaft is connected to a rotary table on which the body (C) is arranged. In addition, the moving shaft is connected to the driving mechanism, which is a gearmotor, through a transmission of helical pinions connected at 90 degrees.

The machine and method described in the present disclosure is not limited to the modalities described and illustrated, since as will be evident to a person skilled in the art, there are variations and possible modifications that do not depart from the spirit of the disclosure, which only It is defined by the following claims.

The invention claimed is:

1. A machine for magnetic stimulation of a tissue, comprising:

a coil that generates a magnetic field;

a first displacement mechanism connected to the coil and to a support surface, where the first displacement mechanism is configured to move the coil in a direction parallel to a longitudinal axis of the tissue until a position of the coil exceeds the length of the tissue and to move the coil away from the tissue;

an angular actuator connected to the coil, the angular actuator being configured to change an orientation of the coil relative to the longitudinal axis of the tissue; and a control circuit connected to the first displacement mechanism and the angular actuator;

where the control circuit is configured to execute a predetermined movement pattern by controlling the first displacement mechanism and the angular actuator in a coordinated sequence, said sequence comprising:

i) moving the coil following a first movement pattern in the direction parallel to the longitudinal axis of the tissue until the position of the coil is beyond a length to which the tissue extends;

ii) changing the orientation of the coil in a manner that an axis of the coil forms a 90-degree angle with the longitudinal axis of the tissue;

iii) moving the coil following a second movement pattern in which the 90-degree angle of the axis of the coil with respect to the longitudinal axis of the tissue is conserved and the coil is gradually moved away from the tissue until the magnetic field no longer stimulates the tissue; and iv) changing the orientation of the coil in a manner that the axis of the coil and the longitudinal axis of the tissue are parallel to each other.

2. The machine of claim 1, wherein the first displacement mechanism is a trolley-guide mechanism that includes:

a first guide connected to the support surface;

a first trolley movably coupled to the first guide; and a first driving mechanism connected to the first trolley;

wherein the first driving mechanism moves the first trolley along the first guide.

3. The machine of claim 1, wherein the first displacement mechanism is connected to the angular actuator by means of a linear actuator, wherein the linear actuator allows the coil to be displaced along an x axis, wherein the x axis corresponds to a longitudinal direction of the tissue.

4. The machine of claim 1, further comprising a second displacement mechanism connected between the first displacement mechanism and the angular actuator; where the second displacement mechanism moves the coil along a y axis, wherein the y axis corresponds to a transverse direction of the tissue.

5. The machine of claim 1, further comprising:

a second displacement mechanism connected between the first displacement mechanism and the angular actuator; and a linear actuator connected between the angular actuator and the second displacement mechanism; wherein the second displacement mechanism moves the coil along a y axis, wherein the y axis corresponds to a transverse direction of the tissue, and the linear actuator allows the coil to be displaced along an x axis, wherein the x axis corresponds to a longitudinal direction of the tissue.

6. The machine of claim 5, further comprising a rotating platform located on the support surface, where said rotating platform is configured to allow the body to be arranged thereon.

7. A method of magnetic tissue stimulation, comprising the following steps:

a) disposing a coil operatively on a tissue of a body;

b) generating a magnetic field by means of the coil; and c) moving the coil, while generating the magnetic field, according to a predetermined movement pattern around the tissue to stimulate said tissue;

wherein in step c, the predetermined movement pattern includes the following sequence of sub-steps:

i) moving the coil following a first movement pattern in a direction parallel to a longitudinal axis of the tissue until a position of the coil is beyond a length to which the tissue extends;

ii) changing an orientation of the coil in a manner that an axis of the coil forms a 90-degree angle with the longitudinal axis of the tissue;

iii) moving the coil following a second movement pattern in which the 90-degree angle of the axis of the coil with respect to the longitudinal axis of the tissue is conserved and the coil is gradually moved away from the tissue until the magnetic field no longer stimulates the tissue; and iv) changing the orientation of the coil in a manner that the axis of the coil and the longitudinal axis of the tissue are parallel to each other.

8. The method of claim 7, wherein, in step b), the magnetic field responds to an activation signal.

9. The method of claim 7, wherein, in step b), the magnetic field generated on the tissue has an intensity between 0.1 mT (milliteslas) and 200 mT.

10. The method of claim 7, wherein sub-step ii) corresponds to removing an electrical supply from the coil.

* * * * *